US010697955B2

(12) United States Patent
Wood et al.

(10) Patent No.: US 10,697,955 B2
(45) Date of Patent: Jun. 30, 2020

(54) METHOD AND SYSTEM FOR DETECTION OF DISEASE AGENTS IN BLOOD

(71) Applicant: MONASH UNIVERSITY, Clayton (AU)

(72) Inventors: Bayden R. Wood, Upwey (AU); Philip Heraud, Clayton (AU); David Perez-Guaita, Clayton (AU)

(73) Assignee: MONASH UNIVERSITY, Clayton, Victoria (AU)

( * ) Notice: Subject to any disclaimer, the term of this patent is extended or adjusted under 35 U.S.C. 154(b) by 0 days.

(21) Appl. No.: 16/208,441

(22) Filed: Dec. 3, 2018

(65) Prior Publication Data
US 2019/0145952 A1      May 16, 2019

Related U.S. Application Data

(63) Continuation of application No. 15/521,206, filed as application No. PCT/AU2015/000631 on Oct. 23, 2015, now Pat. No. 10,145,839.

(30) Foreign Application Priority Data

Oct. 24, 2014   (AU) ............................... 2014904257

(51) Int. Cl.
   *G01J 5/00*        (2006.01)
   *G01N 33/49*       (2006.01)
   (Continued)

(52) U.S. Cl.
   CPC ............. *G01N 33/49* (2013.01); *C12Q 1/689* (2013.01); *C12Q 1/70* (2013.01); *G01N 21/35* (2013.01);
   (Continued)

(58) Field of Classification Search
   CPC .. G01N 33/49; G01N 21/3577; G01N 21/552; G01N 2021/3595; G01N 2333/02;
   (Continued)

(56) References Cited

U.S. PATENT DOCUMENTS 6,254,834 B1 *   7/2001   Anderson ............. B01L 3/5021
                                                           422/548
6,379,920 B1     4/2002   El-sayed et al.
(Continued)

FOREIGN PATENT DOCUMENTS

EP         1454126 A1     9/2004
JP       2001317998 A    11/2001
(Continued)

OTHER PUBLICATIONS

Kim et al., "Use of Fourier Transform infrared spectra of crude bacterial lipopolysaccharides and chemometrics for differentiation of *Salmonella enterica* serotypes," 2005, Journal of Applied Microbiology, vol. 99, pp. 411-417. (Year: 2005).*
(Continued)

*Primary Examiner* — Kiho Kim
(74) *Attorney, Agent, or Firm* — Dorsey & Whitney LLP

(57) ABSTRACT

The invention principally relates to a method of detecting a disease agent in blood, comprising: (i) creating a sample infra-red spectrum representative of the blood, with one or more spectral components, each having a wavenumber and absorbance value; (ii) providing a reference database of spectral models, each model having one or more database spectral components of a wavenumber and an absorbance value, wherein the database spectral components identify disease agents; (iii) determining whether one or more database spectral components corresponds to one or more sample spectral components, and (iv) compiling a list of corresponding database components identified.

10 Claims, 33 Drawing Sheets

(51) Int. Cl.
*G01N 21/552* (2014.01)
*G01N 21/3577* (2014.01)
*C12Q 1/70* (2006.01)
*C12Q 1/689* (2018.01)
*G01N 21/35* (2014.01)
*G01N 33/487* (2006.01)

(52) U.S. Cl.
CPC ....... *G01N 21/3577* (2013.01); *G01N 21/552* (2013.01); *G01N 33/487* (2013.01); *G01N 33/492* (2013.01); *G01N 2021/3595* (2013.01); *G01N 2201/1293* (2013.01); *G01N 2333/02* (2013.01); *G01N 2333/16* (2013.01); *G01N 2333/186* (2013.01); *G01N 2333/445* (2013.01); *G01N 2800/00* (2013.01); *G01N 2800/26* (2013.01)

(58) Field of Classification Search
CPC ......... G01N 2333/16; G01N 2333/186; G01N 2333/445; G01N 2800/26; G01N 2800/00; G01N 33/487; G01N 21/35; C12Q 1/70; C12Q 1/689
See application file for complete search history.

(56) References Cited

U.S. PATENT DOCUMENTS

| | | | |
|---|---|---|---|
| 8,688,384 | B2 | 4/2014 | Puppels et al. |
| 9,024,002 | B2* | 5/2015 | Cummings ............ C12Q 1/689 536/23.1 |
| 10,145,839 | B2 | 12/2018 | Wood et al. |
| 2002/0122168 | A1 | 9/2002 | Garcia-rubio et al. |
| 2008/0113337 | A1 | 5/2008 | Sakudo et al. |
| 2011/0027901 | A1* | 2/2011 | Gaster .................. G01N 27/745 436/149 |
| 2012/0016818 | A1 | 1/2012 | Hackett et al. |
| 2014/0206905 | A1 | 7/2014 | Schiefer et al. |

FOREIGN PATENT DOCUMENTS

| | | |
|---|---|---|
| JP | 2002518670 A | 6/2002 |
| JP | 2003534530 A | 11/2003 |
| JP | 2008523413 A | 7/2008 |
| JP | 2005512644 A | 5/2015 |
| WO | 2006051847 A1 | 5/2006 |
| WO | 2010048678 A1 | 5/2010 |
| WO | 2014076480 A1 | 5/2014 |
| WO | 2015117178 A1 | 8/2015 |

OTHER PUBLICATIONS

Meisel et al., "Raman spectroscopy as a potential tool for detection of *Brucell* spp. in milk," 2012, Applied and Enviromental Microbiology, vol. 78, No. 16, pp. 5575-5583. (Year: 2012).*
Extended European Search Report dated Mar. 29, 2018 for European Application No. 15852707.7
ISA Australian Patent Office, International Search Report Issued in Application No. PCT/AU2015/000631, dated Jan. 11, 2016, WIPO, 3 pages.
Bambery, K. et al., "A Fourier transform infrared microspectroscopic imaging investigation into an animal model ~xhibiting glioblastoma multiforme", Biochimica et Biophysica Acta, vol. 1758, No. 7, Jul. 2006, Published Online May 17, 2006, 8 pages.
Khoshmanesh, Aazam et al., "Detection and Quantification of Early-Stage Malaria Parasites in Laboratory Infected Erythrocytes by Attenuated Total Reflectance Infrared Spectroscopy and Multivariate Analysis," vol. 86, No. 9, pp. 4379-4386, May 6, 2014.
Lasch, P. et al., "Artificial neural networks as supervised techniques for FT-IR microspectroscopic imaging", Journal of Chemometrics, vol. 20, No. 5, Mar. 28, 2007, 20 pages.
Ohta, Koji et al., "Experimental Proof of the Relation between Thickness of the Probed Surface Layer and Absorbance in FT-IR/ ATR Spectroscopy" vol. 39, No. 3; pp. 418-425, May 2, 1985.
Sitole, L. et al., "Mid-ATR-FTIR Spectroscopic Profiling of HIV/ AIDS Sera for Novel Systems Diagnostics in Global Health", OMICS: A Journal of Integrative Biology, vol. 18, No. 8, Aug. 1, 2014, 11 pages.
Webster, G. et al., "Discriminating the Intraerythrocytic Lifecycle Stages of the Malaria Parasite Using Synchrotron FT-IR Microspectroscopy and an Artificial Neural Network", Analytical Chemistry, vol. 81, No. 7, Apr. 1, 2009, Published Online Mar. 11, 2009, 9 pages.
Whelan, D. et al., "Quantification of DNA in simple eukaryotic cells using Fourier transform infrared spectroscopy", Journal of Biophotonics, vol. 6, No. 10, Oct. 2013, Published Online Sep. 18, 2012, 10 pages.
Wood, B. , "Fourier transform infrared (*FTIR) spectral mapping of the cervical transformation zone, and dysplastic squamous epithelium", Gynecologic Oncology, vol. 93, No. 1, Apr. 2004, 17 pages.
Wood, Bayden et al., "Diagnosing malaria infected cells at the single cell level using focal plane array Fourier transform infrared imaging spectroscopy" vol. 139, No. 19, pp. 4769-4774, Published Online Jul. 14, 2014.
English translation of Notification of Reasons for Refusal received in JP Application No. 2017-522334 dated Oct. 1, 2019.
English translation of Office Action received in CN Application No. 201580057790.X dated Apr. 28, 2019.
English translation of Second Office Action received in Chinese Application No. 201580057790.X dated Apr. 7, 2020.

* cited by examiner

METHOD AND SYSTEM FOR DETECTION OF DISEASE AGENTS IN BLOOD

CROSS REFERENCE TO RELATED APPLICATIONS

The present application is a continuation of U.S. application Ser. No. 15/521,206, filed on Oct. 23, 2015, now U.S. Pat. No. 10,145,839, which is a U.S. National Phase of International Patent Application Ser. No. PCT/AU2015/000631, filed on Oct. 23, 2015, which claims priority to Australian Patent Application Serial No. 2014904257, filed on Oct. 24, 2014, the entire contents of which are hereby incorporated by reference in their entirety.

FIELD OF INVENTION

The present invention relates to the field of detection of disease, particularly blood borne disease agents. In a particularly preferred embodiment the present invention relates to detection and quantification of infectious disease in blood.

In one form, the invention relates to a method of using Attenuated Total Reflection Infrared (ATR-IR) spectroscopy for detection, identification and quantification of blood borne disease agents.

In another form, the invention relates to a method of multivariate analysis of data obtained by ATR-IR from blood.

In one particular aspect the present invention is suitable for use for diagnosis of blood borne infectious disease.

In one particular aspect the present invention is suitable for use for diagnosis of malaria, human immune deficiency virus (HIV), or hepatitis B virus (HBV), or hepatitis C virus (HCV) infection from blood samples.

It will be convenient to hereinafter describe the invention in relation to malaria, however it should be appreciated that the present invention is not limited to that use only and can be used for a wide range of other blood borne infectious agents.

BACKGROUND ART

It is to be appreciated that any discussion of documents, devices, acts of knowledge in this specification is included to explain the context of the present invention. Further, the discussion throughout this specification comes about due to the realisation of the inventor and/or the identification of certain related art problems by the inventor. Moreover, any discussion of material such as documents, devices, acts or knowledge in this specification is included to explain the context of the invention in terms of the inventor's knowledge and experience and, accordingly, any such discussion should not be taken as an admission that any of the material forms part of the prior art base or the common general knowledge in the relevant art in Australia, or elsewhere, on or before the priority date of the disclosure and claims herein.

Attenuated Total Reflection Infrared (ATR-IR) Spectroscopy

Spectroscopy is the branch of science devoted to discovering the chemical composition of materials by examining the interaction of electromagnetic radiation with the material. Infrared (IR) spectroscopy relates primarily to the absorption of energy by molecular vibrations having wavelengths in the infrared segment of the electromagnetic spectrum, that is energy of wave number between 200 and 4000 $cm^{-1}$. Raman spectroscopy relates to the inelastic scattering of monochromatic light giving wavelength shifts that depend on the molecular vibrations, having typically wave number shifts between 20 and 4000 $cm^{-1}$.

The structure of almost all biological molecules includes moieties that absorb energy in the IR segment of the electromagnetic spectrum. Thus, an IR spectrum of a clinical sample is representative of its main biological components and can be in the nature of a 'metabolic fingerprint'.

ATR is a sampling technique that can be used in conjunction with IR. ATR spectroscopy offers the advantages of being potentially portable, it is inexpensive and thus has become a very powerful tool in the analysis of biological cells and tissues. ATR also allows samples to be examined directly in the solid or liquid state without further preparation, and compared with transmission-IR, the path length into the sample is shorter, avoiding strong attenuation of the IR signal in highly absorbing media such as aqueous solutions.

In use, the sample is put in contact with the surface of a crystal having a higher refractive index than the sample. A beam of IR light is passed through the ATR crystal in such a way that it reflects at least once off the internal surface in contact with the sample. This reflection forms an evanescent wave which extends into the sample. The penetration depth into the sample depends on the wavelength of light, the angle of incidence and the indices of refraction for the ATR crystal and the medium being probed. The number of reflections may be varied. The beam is then collected by a detector as it exits the crystal.

Viral Hepatitis

Viral hepatitis is caused by one or more of the six unrelated hepatotropic viruses hepatitis A virus, hepatitis B virus, hepatitis C virus, hepatitis D virus, hepatitis E virus and hepatitis G virus. Millions of deaths occur annually around the world due to hepatitis. Diagnosis is made by assessing a patient's symptoms, physical examination and medical history in conjunction with blood tests, liver biopsy and imaging. In many cases patients suffering hepatitis are not aware of symptoms, only becoming aware of the disease during routine blood tests.

But several liver diseases present with signs, symptoms or liver function test abnormalities similar to viral hepatitis. Accordingly, new diagnostic techniques that can rapidly and inexpensively distinguish between these various diseases of the liver are being sought. Preferably, new diagnostic techniques can distinguish between the various hepatitis viruses.

Human Immunodeficiency Virus (HIV)

HIV is a lentivirus that causes acquired immunodeficiency syndrome (AIDS) comprising progressive failure of the immune system. Many patients are unaware they have been infected by HIV and widespread, routine testing does not usually occur even amongst population sectors at high risk of infection.

HIV testing is initially by enzyme-linked immunosorbent assay (ELISA) carried out in duplicate to detect antibodies-positive patients. Confirmatory testing is then carried out with a more specific test (eg Western blot or immunofluorescence assay). If Western blot alone is used, a second specimen is usually collected more than a month later and retested. Nucleic acid testing such as PCR testing can also be performed can also help diagnosis.

Although these established testing regimes are very accurate, they are onerous in terms of time, labour and expense. Accordingly, new diagnostic techniques that can rapidly and inexpensively detect HIV infection are still being sought.

Malaria

Malaria is a mosquito borne disease caused by five parasitic protozoans of the genus *Plasmodium, Plasmodium falciparum, Plasmodium vivax, Plasmodium ovale curtisi, Plasmodium ovale wallikeri, Plasmodium malariae, Plasmodium knowlesi*. There are up to 1.2 million fatalities per annum and accurate and early diagnosis followed by the immediate treatment of the infection is essential to reduce mortality and prevent overuse of antimalarial drugs.

During the course of its life the malaria parasite transgresses through several developmental stages including a sexual and an asexual reproductive pathway. New technologies to diagnose malaria must be cost effective and have high sensitivity and be able to detect circulating stages of the malaria parasite namely the ring and gametocyte forms because these are the only stages present in peripheral blood circulation.

Optimally, the diagnosis of malaria in a patient is followed up by the appropriate antimalarial treatment which must be initiated immediately. Treatment should be guided by three main factors:
  the identify of the infecting *Plasmodium* species;
  the clinical status of the patient; and
  the drug susceptibility of the infecting parasites as determined by the geographic area where the infection was acquired and the previous use of antimalarial medicines Determination of the infecting *Plasmodium* species for treatment purposes is important for three main reasons. Firstly, *Plasmodium falciparum* and *Plasmodium knowlesi* infections can cause rapidly progressive severe illness or death while the other species such as *Plasmodium vivax, Plasmodium ovale*, or *Plasmodium malariae*, are less likely to cause severe manifestations. Secondly, *Plasmodium vivax* and *Plasmodium ovale* infections also require treatment for the hypnozoite forms that remain dormant in the liver and can cause a relapsing infection. Finally, *Plasmodium falciparum* and *Plasmodium vivax* species have different drug resistance patterns in differing geographic regions. For *Plasmodium falciparum* and *Plasmodium knowlesi* infections, the urgent initiation of appropriate therapy is especially critical.

Efforts have also been made to investigate the potential of synchrotron Fourier Transform Infrared (FTIR) in combination with Principal Component Analysis (PCA) to differentiate between intraerythrocytic stages or the parasite life cycle based on the molecular signatures of Hz and specific lipids (Webster et al. Disciminating the Intraerythrocytic Lifecycle Stages of the Malaria Parasite Using Synchrotron FT-IR Microspectroscopy and an Artificial Neural Network, Analytical Chemistry 2009, 81, 2516-2524). Webster et al found that as the parasite matures from its early ring stage to the trophozoite and finally to the schizont stage there is an increase in absorbance and shifting of specific lipid bands.

This work demonstrated the potential of using FTIR spectroscopy as a diagnostic tool for malaria but clearly a synchrotron-based method is not suitable for field use or for routine laboratory use.

FTIR spectroscopic diagnosis relies on precise acquisition of spectra, spectral pre-processing and chemometric tools such as Artificial Neural Network analysis (Lasch et al., J. Chemometr. 20, 209-220 (2006)) or Unsupervised Hierarchical Cluster Analysis (Bambery et al., Biochim. Acta. 1758, 900-907 (2006); Wood et al., Gynecol. Oncol. 93, 59-68 (2004)).

There is enormous spectral variation between biological samples caused by a number of factors, including spectral scatter caused by preparative techniques and scattering artifacts which have hindered progress of FTIR as a clinical diagnostic tool. Furthermore, the some biological moieties have infra-red molar absorptivity characteristics that do not comply with Beer-Lambert law.

FTIR spectroscopic methods have also been used for the detection of cancerous and precancerous cells and tissues (Whelan et al., J. Biophotonics 6, No. 10, 775-784 (2013)/ DOI 10.1002/jbio.201200112). In order to overcome non-Beer-Lambert infra-red absorption behaviour, simple statistical models were developed to predict the concentration of DNA in cells. However it is acknowledged in this study that the simple models developed from the study would not be adequate for complicated cells or complex mixtures of biological compounds.

In another study (Sitole et al, OMICS A J. Integrative Biol. 18(8) 513-523 (2014), mid-ATR-FTIR spectroscopic profiling of blood sera has been explored as a diagnostic for HIV/AIDS. While the system is judicative of the promise for diagnosis it is clear that problems arise with the data used due to modelling based on artifactual differences. In particular separation is observed in loadings plots due to differences in bound water and artefacts resulting due to a lack of ATR correction on the spectra.

Accordingly, there is a need for new methods to enable wider use of FTIR as a diagnostic.

SUMMARY OF INVENTION

An object of the present invention is to provide a method suitable for detecting identifying and quantifying blood borne infectious disease agents.

An object of the present invention is to provide a method suitable for field use or laboratory use for detecting and quantifying bipod borne infectious disease.

An object of the present invention is to provide a method suitable for detecting and quantifying blood borne infectious disease agents in a sample of whole blood, or plasma, or blood cells, or dried whole blood.

A further object of the present invention is to alleviate at least one disadvantage associated with the related art.

It is an object of the embodiments described herein to overcome or alleviate at least one of the above noted drawbacks of related art systems or to at least provide a useful alternative to related art systems.

In a first aspect of embodiments described herein there is provided a method of detecting a disease agent in a blood sample, the method comprising the steps of:
  (i) creating an infra-red sample spectrum representative of the blood sample, the sample spectrum having one or more spectral components, each component having a wavenumber and absorbance value,
  (ii) providing a reference database of spectral models, each model having one or more database spectral components of a wavenumber and an absorbance value, wherein the database spectral components identify disease agents,
  (iii) determining whether the reference database has one or more database spectral components corresponding to one or more sample spectral components, and
  (iv) compiling a list of corresponding database components identified.

Preferably, step (ii) of the method further includes selecting one or more spectral windows in which to undertake step (iii).

Typically the IR spectrum is created by delivering an evanescent IR beam through an ATR substrate in contact with a patient blood sample. This can be obtained putting or drying the sample on the ATR or from a thick blood film on a slide, such as a glass or plastic slide. Other alternative is to obtain the, the IR spectrum is created using focal plane array, that is, focal plane spectroscopic imaging of thin blood smears on glass.

Most laboratories in the developing world currently use thick blood films on slides for routine microscopy. It is therefore particularly advantageous that the method of the present invention can be used to analyse thick films on slides without changing the current laboratory methodology. Furthermore, the method of the present invention can be used to detect disease agents in archived thick film blood samples.

The present invention also advantageously provides the option of using a minimal volume of blood, such as a single drop of less than 50 µl, more preferably between 5 and 25 µl. Most infectious disease diagnostic techniques require far larger volumes of blood.

In one particular aspect the present invention is suitable for use for diagnosis of human immune deficiency virus (HIV), or hepatitis B virus (HBV), or hepatitis C virus (HCV) infection from blood samples or other blood borne viral diseases including viral haemorrhagic viruses which includes and is not limited to viruses of several viral families including Arenaviridae (Lassa fever, Junin and Machupo), Bunyaviridae (Crimean-Congo haemorrhagic fever, Rift Valley Fever, Hantaan haemorrhagic fevers). Filoviridae (Ebola and Marburg) and Flaviviridae (yellow fever, dengue, Omsk haemorrhagic fever, Kyasanur forest disease, West Nile virus), viruses that are transmitted by arthropods or vectors such as those of the Alphaviridae. Other blood borne infectious diseases of man may be transmitted by parasites which includes malaria (including differentiation between the various phases of malaria and various species). African trypanosomiasis, babesiosis, Chagas disease, leishmaniasis, and toxoplasmosis. Parasitic blood borne agents includes Babesia *B. divergens, B. bigemina, B. equi, B. microfti, B. duncani, Leishmania Toxoplasma gondii, Plasmodium falciparum, Plasmodium vivax, Plasmodium ovale curtisi, Plasmodium ovale wallikeri, Plasmodium malariae, Plasmodium knowlesi, Trypanosoma brucei* and *Trypanosoma cruzi*.

Blood Sample

The patient blood sample may be in any convenient form, such as whole blood, plasma, blood cells, dried whole blood or combinations thereof. Preferably the blood sample is whole blood and can be collected by a simple finger prick and delivered directly to an IR spectrometer, or onto a glass or plastic slide.

But whole blood is not always optimal for diagnosis of a particular disease. The form used will depend on a wide range of factors including convenience and the availability of apparatus for processing whole blood. In particular it should be noted that variation in IR spectra relating to a specific disease can be due to other factors not associated or relevant to the disease. Those factors can mask the absorbances or patterns of interest and make it difficult to compile a list of sample components corresponding to a spectra model in the database.

Accordingly, it may be necessary to carry out a simple whole blood pre-processing step to eliminate uncorrected components such as water ('dry' sample), cells (serum sample), proteins and polar compounds (organic extracted sample) or isolate the compounds of interest such as white blood cells or lipids. Carrying out a pre-processing step can make possible the diagnosis of a disease otherwise undetectable by direct measurement of a whole blood sample.

Preferably the blood sample is 'wet', that is in a liquid form and not dried. The "wet" blood sample in one form may contain a solvent that is naturally occurring, such as water—or deliberately added, such as methanol.

Wet samples include, for example, whole blood collected by a finger prick from a patient. In the field the whole blood sample may be lysed and solvent added, usually water. Alternatively, the whole blood may be fractioned to isolate plasma. Typically, fractionation would be carried out in a laboratory where suitable equipment is readily available rather that in the field. For example, the whole blood sample may be extracted with a solvent such as chloroform to extract lipid bilayers for analysis.

As a less preferred alternatively to wet samples, the patient blood sample may be 'dry' that is, having naturally occurring or added solvent driven off by drying in air, under a heat lamp or by another drying process.

Spectral Components Identifying Disease Agents

Disease agents present in the blood, such as infectious agents include biological moieties that absorb energy to create a signal in the mid-IR range. The energy may be absorbed directly by a disease agent—such as a virus present in the blood. Alternatively the energy may be absorbed by other biological entities which are indicative of the presence of the disease agent. Metabolic changes caused by some disease agents can lead to elevated blood levels of species such as glucose or urea, thus indirectly indicating the presence of a disease agent.

For example, if the disease agent is malaria, the blood sample will exhibit IR absorption bands associated with the molecular phenotype of malaria which is all the molecular and chemical components associated with the infectious agent generated during the reproduction cycles of the malaria parasite. Other indirect absorption may occur due to the disease agent modifying the metabolic state of the patient including modifying the host cells and its response to an infectious agent. Importantly the present invention is potentially capable of distinguishing between the five parasitic protozoans of the genus *Plasmodium*. For example, tests using *Plasmodium falciparum Plasmodium vivax* and *Plasmodium malariae* have confirmed that spectral differences can be detected between these three species and the method of the present invention can distinguish between them.

Each virus and/or infectious agents have unique characteristics such as for HIV these particles contain single-strand RNA which tightly bound to nucleocapsid proteins, late assembly protein, and enzymes essential to the development of the virion, such as reverse transcriptase and integrase. There will be also unique replicative forms within cells for infectious agents capable of infecting cellular components within blood cells. For example, HIV infects vital cells in the human immune system such as helper T cells (specifically CD4+ T cells), macrophages, and dendritic cells.

As such there is the potential to detect IR absorption bands that correspond to the molecular phenotype for each infectious agent and includes viral replicative intermediates, "free" viral particles and also the changes to the infected cells. Other blood borne infections agents may not be actively replicating within whole blood but virus particles or other viral components may be found within the blood such as for hepatitis B virus in which three forms are found. The most abundant are small, spherical, noninfectious particles, containing HBsAg, that measure 17 to 25 nm in diameter. Concentrations of 1013 particles per ml or higher have been detected in some sera. Tubular, filamentous forms of various lengths, but with a diameter comparable to that of the small particles, are also observed. They also contain HBsAg polypeptides. The third morphological form, the 42 nm hepatitis B virion.

The following table (Table 1) and FIG. 3 show typical IR bands of biological compounds and their respective assignments. The presence of an infectious disease in the blood can be directly or indirectly related to the IR spectra through those bands.

TABLE 1

| Wavenumber (cm$^{-1}$) | Assignment | Analytes | Referenced to FIG. 3 |
|---|---|---|---|
| 930-1300 | $\nu_s$ (C—O) | Saccharides | 140 |
| 1000-1150 | $\nu_s$ (P—O) | Phospholipids, DNA | 140 |
| 1150-1300 | $\nu_{as}$ (P—O) | Phospholipids, DNA | 140 |
| 1200-1400 | Amide III | Proteins | 103, 150 |
| 1430-1480 | $\delta(CH_3)$, $\delta(CH_2)$ | Lipids | 130 |
| 1480-1600 | Amide II | Proteins | 102, 150 |
| 1600-1720 | Amide I | Proteins | 101, 150 |
| 1700-1760 | $\nu_s$ (C=O) | Lipids | 120 |
| 2840-2860 | $\nu_s$ (CH$_2$) | Lipids | 110 |
| 2860-2870 | $\nu_s$ (CH$_3$) | Lipids | 110 |
| 2870-2950 | $\nu_{as}$ (CH$_2$) | Lipids | 110 |
| 2950-2990 | $\nu_{as}$ (CH$_3$) | Lipids | 110 |
| 3000-3020 | $\nu$ (CH) | Lipids | 110 |
| 4000-4550 | $\nu$ (CH) combinations | Lipids | 110 |
| 4550-5000 | $\nu$ (NH) $\nu$ (OH) combinations | Proteins, saccharides | |
| 5600-6050 | 1° overtone $\nu$ (CH) | Lipids | |
| 6700-7150 | 1° overtone $\nu$ (NH) $\nu$ (OH) | Proteins, saccharides | |
| 8000-9100 | 2° overtone $\nu$ (CH) | Lipids | |
| 9100-10500 | 2° overtone $\nu$ (NH) $\nu$ (OH) | Proteins, saccharides | |
| 11520-11760 | 3° overtone $\nu$ (CH) | Lipids | |
| 11765-12900 | 3° overtone $\nu$ (NH) | Proteins, saccharides | |

For example, FIG. 19 illustrates an IR spectrum of a whole blood sample with a high viral load of HIV after subtraction of control spectra. Differences have then been enhanced and the spectrum can be divided up as follows:

(A) The absorption bands at approx. 1010 to 1050 cm$^{-1}$ and approx. 1140 to 1190 cm$^{-1}$ are enhanced in the case of a virus. Since they are assigned to RNA and DNA they are potentially attributable to the virus itself (direct relationship).

(B) The absorption band at approx. 1380 to 1410 cm$^{-1}$ is also enhanced in the case of a virus. It is difficult to establish their origin but it is not a typical nucleic absorption band, and is due to the influence of the virus on other metabolites (indirect relationship).

(C) The absorption bands in the regions of approx. 1060 to 1150 cm$^{-1}$, approx. 1195 to 1340 cm$^{-1}$ and approx. 1410 to 1690 cm$^{-1}$, often show different patterns for different samples. Therefore they are not connected with the presence of a virus. They may be associated with other biological factors not associated with disease states.

Thus, HIV can be identified according to bands (A) and (B). However spectral features of (C) not associated with the disease could dominate given the enormous natural variation in blood samples. Accordingly, it can be difficult to obtain sufficient sensitivity and specificity if a single wavenumber were relied upon for detection and it is preferable to look for a pattern in the spectrum using machine learning algorithms.

Spectral Models

The aforementioned pattern is typically found through a model expressed in terms of the range of operations expected to be performed by the classification function (that is the possible g(x) of f=g(x)). An algorithm is a mathematical procedure (normally iterative) employed for establishing g(x). In the present invention, the model consists of an algorithm ($Y_{Presence\ of\ the\ disease} = f(X_{Spectrum})$) establishing the mathematical relationship between the spectrum (X) of a blood sample and some attribute of the blood sample (Y), that is, spectral components identifying the disease agents.

FIG. 20 is a flow chart illustrating how spectra with, and without the disease are input to the algorithm, to learn the characteristic spectral components of the spectra for each class (positive for presence of the disease, negative or unknown) to thus form a 'calibration matrix'. From this is provided a set of mathematical operations that can be applied to the spectrum (a vector of absorbance values) for a new blood sample to generate a value that determines if the spectrum can be classified as positive, negative or unknown.

A model may be specific for one specific disease agent (eg separate models for HIV and Hepatitis B virus) or combinations of disease agents. Models of combinations are particularly useful for two or more disease agents that are frequently identified together (eg HIV+Hepatitis B virus).

Algorithms for Classifications

Algorithms suitable for use in the present invention include, but are not limited to the following:

Linear modelling (LDA, PLSDA, SIMCA);
Neural Network analysis (NNA);
Random Forest (RF);
Supported Vector Machine (SVM).

Typically, the performance of all the algorithms for each dataset is independently investigate. The selection of the best modelling system is based normally in the prediction results obtained. It is also possible to use aggregation models (that is, for each sample each modelling system gives a vote for a class and the final prediction is obtained by computing the mode of those votes).

It is noted there are no "best models" established for the diagnosis of a particular disease agent. Depending on different factors inherent in the disease agent, the number of samples and the variability of those samples, some algorithms show more classification performance than others. Accordingly, for each application a prior deep study of the different modelling possibilities should be performed. Optimally, all the variables involved in the modelling should be established.

Some pre-processing of the spectra may be carried out to prepare them for the modelling in order to improve the model performance.

As described below, selection of a set of wavenumbers can enable a better classification performance.

Other variables that may be optimised to create a useful model include the number of trees in the RF and latent variables in the PLSDA.

In a second aspect of embodiments described herein there is provided a method of creating a spectral model for use in a reference database of spectral models for detecting a disease agent in a blood sample, the method comprising the steps of:

(i) collecting calibration infra-red spectra representation of blood samples carrying the disease agent and blood samples absent the disease agent, the calibration spectra having one or more spectral components, each component having a wavenumber and absorbance value; and (ii) creating an algorithm $Y_{Presence\ of\ the\ disease}=f(X_{Spectrum})$ establishing the relationship between the spectrum (X) of said blood samples and the spectral components of the blood samples (Y) that identify the disease agent.

Creation of a Model

Step typically used in the creation of a suitable model include the following and are illustrated in FIG. 23:

Obtaining a Sample Set:

A set of blood samples and their reference data (that is, whether they are positive or negative for a given disease agent) are collected. IR spectra of the blood samples are recorded and used to create a matrix X (n=number of samples x v=number of wavenumbers) and a vector of reference data Y (nx1). The blood samples are classified in 3 different subsets: calibration, validation and test set.

Preprocessing of the Spectra:

Mathematical operations may be performed on the aforementioned spectra prior to the modelling with the aim of removing extraneous external sources of variation and enhancing the differences of the spectra connected with the bands of interest. These mathematical operations include, for example:

correction of baseline shifts and path length changes,
correction of spectral artefacts related to the experimental procedure (atmospheric contributions, scattering or ATR correction), and
enhancement of the difference of the bands, especially in the maximum position of the bands, among spectra by the use of derivatives or mean centering.

Variable Selection Procedure:

Non-informative parts of the spectra may be removed in order to improve the accuracy of the classification. In particular, it is preferable to use a limited number of wavenumbers (selected spectral windows) that are relevant to a particular disease. For example for some disease agents the informative part of the spectrum may be the C-H(stretch) characterising lipids at 3100 to 2700 cm$^{-1}$. For proteins, nucleic acids and carbohydrates the informative part of the spectrum may be from 1800 to 900 cm$^{-1}$. The informative window of the spectrum for moieties exhibiting amide 1, 2 or 3 stretching modes are more likely to be at 1800 to 1200 cm$^{-1}$.

It is possible to use multiple spectral windows and process them sequentially or simultaneously.

The use of two or more selected spectral windows typically improves the accuracy of results obtained using the model. For example FIGS. 24 to 27 illustrate PLS-DA performed (as described below) on a sample of red blood cells (fixed with methanol) using one spectral window (FIGS. 24 and 25) and two spectral windows (FIGS. 26 and 27), using samples positive for malaria, and control samples.

Specifically, FIGS. 24 and 25 relate to use of the spectral window corresponding to lipids associated with malaria and correspond to Confusion Table (CV) (Table 2):

TABLE 2

|  | Control | Actual Malaria |
| --- | --- | --- |
| Predicted as Control | 10 | 11 |
| Predicted as Malaria | 3 | 84 |

FIGS. 26 and 27 relate to use of the spectral window corresponding to lipids associated with malaria in addition to the spectral window corresponding to the C-O and P-O region for malaria and correspond to Confusion Table (CV) (Table 3):

TABLE 3

|  | Control | Actual Malaria |
| --- | --- | --- |
| Predicted as Control | 13 | 1 |
| Predicted as Malaria | 0 | 92 |

Clearly the use of one window resulted in some false positives and some false negatives, but the performance of the model is improved when two spectral windows are used.

Modelling:

After the aforementioned pre-processing and variable selection steps, only calibration data is employed for building the model. The algorithm is applied and a function $y=f_{selected(x)}$ is established. This process could also serve to set-up some internal parameters of the model.

Optimisation of Parameters:

In this step the function is applied to the spectra of a validation set of samples. The $Y_{val}$ returned by the function is compared with the one of the reference data, thus identifying any classification error. At this point the parameters (pre-processing, variable selection, type of model, algorithm, and other variables) can be changed and the new f(x) can be obtained, with a corresponding associated error. One of the functions (and associated parameters) having a classification performance which fulfils the requirements of the application can be selected $y=f_{selected(x)}$. Thus, the validation set is used only to tune all the parameters involved in the modelling, created using the training set.

It will be readily apparent to the person skilled in the art that the process may be iterative, but selection of the parameters can also be carried out by various other approaches, or combinations of approaches including:

using the knowledge the character of the analytical problem; for example, if the model is not linear, PLSDA is not used or CO$_2$ region is not used for classification, and using Iterative procedures (for example a genetic algorithm in the variable selection).

Optimisation:

The optimisation step comprises: calculation of the classification error using all the possible values of the variables for example, and selection of the latent variables in the PLSDA. This procedure can also be performed using the CV of the training set if the number of samples is limited and a validation set is not available.

Testing the Model:

The actual classification capability of the function selected in the Modelling step is then evaluated using and independent test of samples (that is, the $X_{test}$ spectra of the test samples is introduced as an input in the function and the output $Y_{test}$ is compared with the reference data $Y_{test}$. The error value is the expected error of the classification. If assumable, the model is ready to be used in a new patient blood sample of unknown disease status.

Diagnosis of a New Sample:

Once the appropriate $y=f_{selection(x)}$ is established with known error limitations, it can be applied to a spectrum of a new sample from a patient to determine a response (positive and negative).

It will be readily appreciated that the method used also requires monitoring to ensure ongoing accuracy. This can be carried out using control samples which can be predictive of future changes in the model.

FIG. 21 illustrates a preferred embodiment of model creation, and application to a blood sample having an unknown disease status. The model may be linear or nonlinear. But in this preferred embodiment, a linear model is created based on discriminant analysis by partial least squares algorithm (PLS DA), to provide a vector of weights of each wavenumber (i), the 'regression vector':

$$W=(w_1, w_2, w_3 \ldots w_i)$$

As described previously, it is preferable to use a limited number of wavenumbers (selected band widths) that are relevant to a particular disease. There are various ways to select those wavenumbers, from the straightforward selection of the regions of interest to complex iterative selections such as genetic algorithm.

Considering the spectra as a vector of absorbance values:

$$X=(x_1, x_2, x_3 \ldots x_i)$$

The final outcome is calculated by multiplying the regression vector W(i) by the absorbance values of the spectrum at each absorbance X(i):

$$Y=w_1x_1+w_2x_2+w_3x_3 \ldots w_ix_1)$$

Y values close to +1 are assigned to one class (eg positive for the disease agent) and Y values close to 0 are assigned to the other class (eg negative for the disease agent). It will be appreciated that the cut-off values relating to assignment to one class or the other are arbitrary and is one of the variables that can be optimised, or altered. This might be appropriate for example, if it is preferred to have more false positives than false negatives.

Accordingly, the method of the present invention may include a further step of allocating or flagging a blood sample as being positive for a disease, negative for a disease, or of unknown disease state. Thus the further step may comprise:

(iv) determining the number of sample components in each respective spectral model compiled and ranking said compiled spectral model.

Alternatively, the further step may comprise:

(iv) determining the number of sample components in each respective spectral model compiled and classifying said compiled spectral model based on predetermined classification criteria.

FIG. 22 includes a flow chart depicting the method of the present invention for creating a model to classify samples as positive or negative for hepatitis viruses (Hep) that includes hepatitis B virus (HepB) and Hepatitis C virus (HepC). The model according to the present invention can be used to identify a specific hepatitis virus (hepatitis A, hepatitis B, hepatitis C, hepatitis D, hepatitis E, hepatitis G) or combinations of hepatitis viruses.

Specifically, FIG. 22 reflects calibration using 10 blood samples (serum samples) loaded with HepB, 10 serum samples loaded with HepC and 11 serum samples loaded with HIV. The preprocessing steps include calculation of a first derivative and mean centering. The variable selection step consist of choosing an appropriate fingerprint area (900~1750 cm$^{-1}$).

A PLS model is then combined with a NINPALS algorithm, an interative algorithm used in PLS for obtaining the weights of regression vectors. Another parameter used is the number of LV(4) Y=fselected(x): Regression vector.

The validation step is carried out using a limited set of samples (rather than the validation set available) with cross validation. As indicated in FIG. 22 two samples (sample nos 22 and 33) are used to test the model. (NB: This is for illustration only. Typically far more samples would be used to test the model.) Once the model is suitable for classifying 100% of samples it is ready to be used to classify the status of an unknown blood sample from a patient.

FIG. 20 illustrates how in a first step are created calibration spectra are collected using blood samples known to be loaded or free of a disease agent. A reference database of spectral models is defined by a regression vector. An IR spectrum representative of a new blood sample (presence of disease agent unknown) is created and applying said spectrum to a reference database of spectral models to identify one or more spectral components of wavenumber and absorbance of the blood sample. The spectral components identify disease agents in this case as either hepatitis virus (HBV or HCV) or HIV. A list of sample components is identified corresponding to a respective spectral model of the database. Finally the new blood sample is classified as positive or negative with respect to hepatitis virus (HBV or HCV) or HIV.

System & Device

The generation of spectral models, preparation of calibration spectra from known blood samples knows to positive or negative for a specific disease agent can be carried out in a laboratory. Once these are generated the algorithm and model function can be incorporated into a software application (app) and forwarded wirelessly to a user.

Thus in another embodiment the present invention provides a computer readable storage medium for storing in non-transient form an application for executing a method of detecting a disease agent in a blood sample, comprising the steps of:

(i) recording an IR spectrum representative of the blood sample;

(ii) comparing said spectrum to a reference database of spectral models to identify one or more spectral components of wavenumber and absorbance of the blood sample, wherein the spectral components identify disease agents; and (iii) compiling a list of sample components identified corresponding to a respective spectral model of the database;

wherein steps (i) to (iii) are automated.

It will be clear to the person skilled in the art that in addition to the application being stored on a computer readable storage medium, it may be stored in the cloud or other computing equivalent. There is thus provided an application adapted to enable the detection of a disease agent in a blood sample, said application comprising a predetermined instruction set adapted to enable a method comprising the steps of:

(i) creating a sample infra-red spectrum representative of the blood sample, the sample spectrum having one or more spectral components, each component having a wavenumber and absorbance value, (ii) providing a reference database of spectral models, each model having one or more database spectral components of a wavenumber and an absorbance value, wherein the database spectral components identify disease agents, (iii) determining whether the reference database has one or more database spectral components corresponding to one or more sample spectral components, and (iv) compiling a list of corresponding database component identified.

Thus, to operate the method of the present invention it is only necessary to have a means for generating an IR spectrum of a patient blood sample (such as a standard FT-IR spectrometer and a diamond crystal ATR accessory) and the model function to derive a diagnosis. This means that the method of the present invention can adapted to a relatively small size that is suitable for field use, even in remote locations.

Thus in a further embodiment, the present invention provides a system for detecting a disease agent in a blood sample, the system comprising a spectrometer for capture of an IR spectrum and a computer,
wherein
(i) the spectrometer creates an IR spectrum representative of the blood sample,
(ii) the computer applies said spectrum to a reference database of spectral models to identify one or more spectral components of wavenumber and absorbance of the blood sample, wherein the spectral components identify disease agents, and
(iii) the computer compiles a list of sample components identified corresponding to a respective spectral model of the database.

Other aspects and preferred forms are disclosed in the specification and/or defined in the appended claims, forming a part of the description of the invention. In essence, embodiments of the present invention stem from the realization that patterns of absorbance within IR spectra of blood samples can be reviewed using machine learning algorithms or the like and used to identify the presence or absence of disease states.

Advantages provided by the present invention comprise the following:
rapid detection of infection facilitating rapid treatment;
rapid identification of infectious agent present in vivo;
a straightforward, low cost diagnostic method;
a method that can use existing equipment;
can be used with existing blood sample collection techniques such as the use of thick film slide samples;
can be used for the detection of a wide range if disease agents including HIV, hepatitis A virus, hepatitis B virus, hepatitis C virus, hepatitis D virus and hepatitis E virus, hepatitis G virus or other blood borne viral diseases including viral haemorrhagic viruses which includes and is not limited to viruses of several viral families including Arenaviridae (Lassa fever, Junin and Machupo), Bunyaviridae (Crimean-Congo haemorrhagic Fever, Rift Valley Fever, Hantaan haemorrhagic fevers), Filoviridae (Ebola and Marburg) and Flaviviridae (yellow fever, dengue, Omsk haemorrhagic fever, Kyasanur forest disease, West Nile virus), viruses that are transmitted by arthropods or vectors such as those of the Alphaviridae. Parasitic blood borne agents includes Babesia *B. divergens, B. bigemina, B. equi, B. microfti, B. duncani, Leishmania Toxoplasma gondii, Plasmodium falciparum Plasmodium vivax, Plasmodium ovale curtisi, Plasmodium ovale wallikeri, Plasmodium malariae, Plasmodium knowlesi, Trypanosoma brucei* and *Trypanosoma cruzi;*
can distinguish between similar or closely related agents present in a blood sample;
can utilise a minimal volume (droplet) or blood.

Further scope of applicability of embodiments of the present invention will become apparent from the detailed description given hereinafter. However, it should be understood that the detailed description and specific examples, while indicating preferred embodiments of the invention, are given by way of illustration only, since various changes and modifications within the spirit and scope of the disclosure herein will become apparent to those skilled in the art from this detailed description.

BRIEF DESCRIPTION OF THE DRAWINGS

Further disclosure, objects, advantages and aspects of preferred and other embodiments of the present application may be better understood by those skilled in the relevant art by reference to the following description of embodiment taken in conjunction with the accompanying drawings, which are given by way of illustration only, and thus are not limitative of the disclosure herein.

The figures relate to the following:

FIG. 5 is an ATR-FTIR spectrum of whole blood, including a control sample (35), and samples having different loads of HIV (36) and Hepatitis C virus (37).

FIG. 6 is an ATR-FTIR spectrum of samples having HIV loading including a control sample (40), whole blood (41) and serum (42).

FIG. 7 is an ATR-FTIR spectrum of a control and serum sample loaded with hepatitis B virus.

FIG. 8 is an ATR-FTIR spectrum of a control, whole blood and serum samples loaded with hepatitis C virus.

FIGS. 9A, 9B and 9C are plots depicting the result of a multivariate analysis showing samples/scores of HIV in WB (□), hepatitis C virus in WB(▲), hepatitis B virus in serum (▼), Hepatitis C virus in serum (*) and HIV in serum (○) against a control (◇). Multivariate analysis is used to clarify differences or find hidden patterns. The method selected is principal components analysis (PCA), an unsupervised method (i.e., it does not take into account the classes, only uses the spectra) that projects the samples in new coordinates orientated in the directions of the variance. In the scores of the PCA performed over the whole set of data, the two first scores space show separation among the serum (56) and whole blood (57) and in particular, among HIV (58) and hepatitis (60) virus samples.

FIG. 14 is an ATR-FTIR plot that allows comparison of spectra from infected WB (73, 74) and control (75) using dry WB samples.

FIG. 15 is an ATR-FTIR plot that allows comparison of spectra from infected WB (77) and controls (78) using wet lysed blood samples.

FIG. 16 is an ATR-FTIR plot that allows comparison of spectra from infected WB (80) and controls (81) using dry lysed blood samples.

FIG. 17 shows an expansion of the region from 1700 to 1728 cm$^{-1}$. A shift of the carbonyl band can be clearly seen, reflecting the spiking level.

DETAILED DESCRIPTION

The present invention will be further described with reference to the following examples of protocols suitable for obtaining samples suitable for ATR-IR analysis.

1. General Procedure for Crystal Cleaning

In general, the ATR crystal is cleaned using the following steps:
a) Humidified Soft cellulose is employed for eliminating the sample.
b) The ATR Crystal is cleaned using soft cellulose and water and/or organic solvents.
c) A spectrum of the empty crystal is obtained in order to discard any memory effect.
d) If proteins are difficult to remove, it is recommended the use of PBS, detergents or micellar water.

2. General Procedures for Sample Preparation 2.1 Whole blood (WB) Sampling Method Whole blood is extracted from the patient in EDTA tubes or directly with a lancet.

2.1.1 Wet WB

Figure 1:
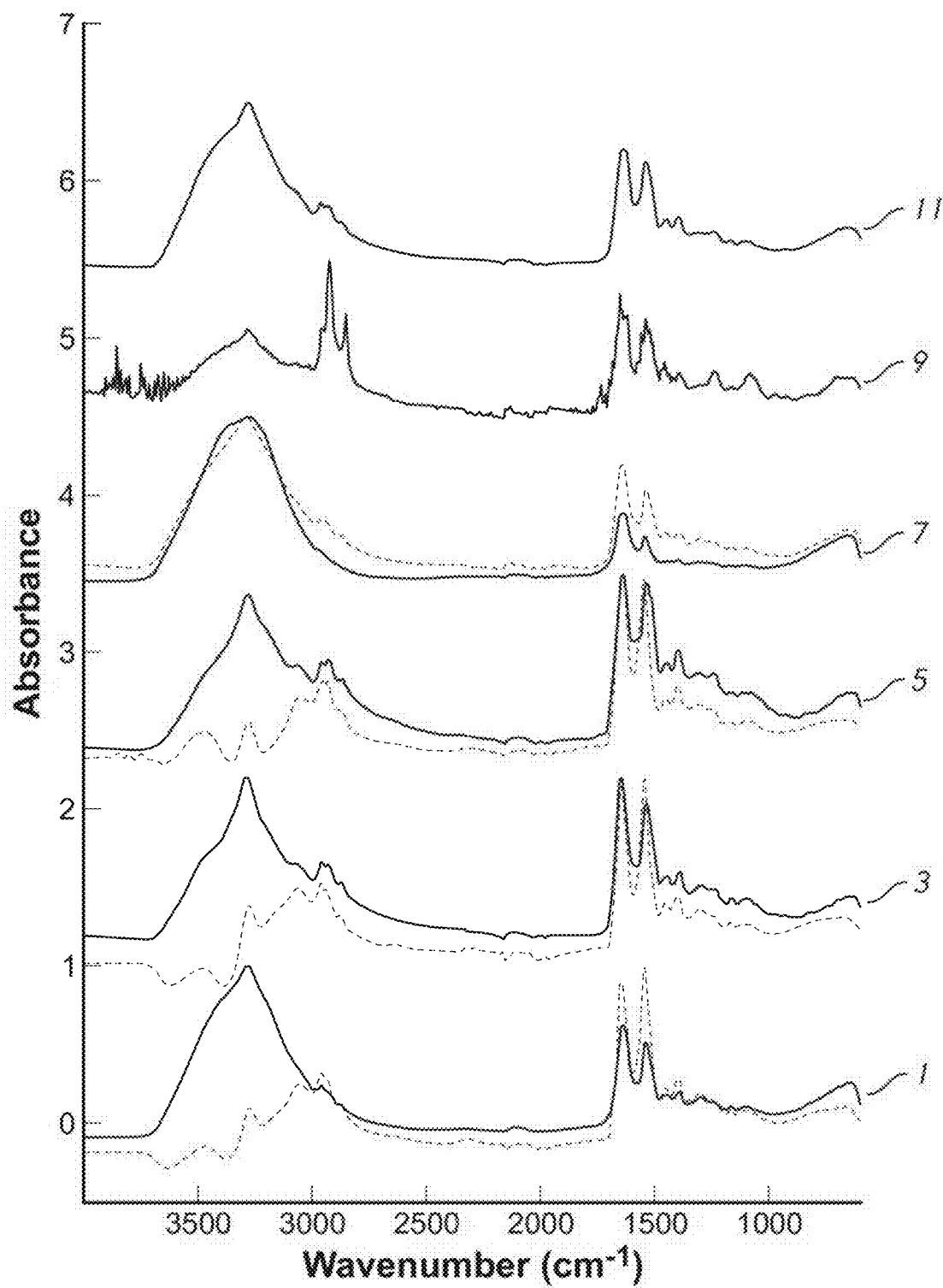
FIG. 1 displays are spectra obtained from different sets of samples; whole blood (1), lysed whole blood (3), plasma (5), RBC (7), RBC in methanol (9), and slurry of coagulated blood (11).

A wet whole blood sample is typically processed according to the method of the present invention to generate the ATR-FTIR spectrum similar to those shown in FIG. 1 using the following steps:
a) A background is obtained using the empty clean ATR crystal.
b) A blank of water (W) is obtained by measuring the spectrum of 10 microliters of water.
c) 10 microliters of the EB are taken with a micropipette and deposited on the surface of the ATR crystal.
d) Raw spectrum of whole blood (RWB) is immediately acquired.
e) The final spectrum ($WB_w$) of the whole blood is obtained by subtracting the intensity of the i wavenumber of W from the i wavenumber of RWB.

$$WB_w(i)=RWB(i)-W(i)$$

f) Crystal is cleaned according to the General Procedure.

2.1.2 Dry WB

A dry whole blood sample is typically processed according to the method of the present invention to generate the ATR-FTIR spectrum shown in FIG. 1 using the following steps:
a) A background is obtained using the empty clean ATR crystal.
b) Between 1 and 5 microlitres (the amount depending on the application) are taken with a micropipette and deposited on the surface of the ATR crystal.
c) Sample is dried through different methods (Allowing to dry/using a drier or heat lamp)
d) After drying, spectrum ($WB_d$) of the whole blood is acquired.
e) Crystal is cleaned according to the General Procedure set out above.

2.2 Lysed WB Sample Method

WB samples are obtained in the same procedure as described above and are lysed by mixing whole blood with distilled water in a ratio 1:1 (v/v) or with a 7% (w/v) sodium dodecyl sulfate (SDS) solution at a ratio 8:1 (v/v).

2.2.1 Wet Lysed WB

A wet lysed whole blood sample is typically processed according to the method of the present invention to generate the ATR-FTIR spectrum shown in FIG. 1 using the following steps:
a) A background is obtained using the empty clean ATR crystal.
b) A bland of water (W) is obtained by measuring the spectrum of 10 microliters of distilled water or a blank of 7% (w/v) SDS solution, mixed with distilled water at a ratio 8:1 (v/v), depending on the method used on the lysis.
c) 10 microliters of lysed WB are taken with a micropipette and deposited on the surface of the ATR crystal. Raw spectrum of plasma (RL) is immediately obtained.
d) The final spectrum ($L_w$) of the lysed whole blood is obtained subtracting the intensity of the i wavenumber of W to the i wavenumber of RL.

$$L_w(i)=RL(i)-W(i)$$

e) Crystal is cleaned according to the General Procedure set out above.

2.2.2 Dry Lysed WB

A dry lysed whole blood sample is typically processed according to the method of the present invention to generate the ATR-FTIR spectrum shown in FIG. 1 using the following steps:
a) A background is obtained using the empty clean ATR crystal.
b) 1-5 (Depending on the application) microliters of lysed WB are taken with a micropipette and deposited on the surface of the ATR crystal.
c) Sample is dried through different methods (Allowing to dry/using a drier or heat lamp)
d) After drying, spectrum ($L_d$) of the plasma is acquired.
e) Crystal is cleaned according to the General Procedure set out above.

2.3 Plasma (P) Sample Method.

Patient plasma samples are typically prepared by first extracting whole blood from the patient in ethylene diamine tetra acetic acid (EDTA) containing tubes or (or serum tubes if serum is required) directly with a lancet. WB samples are centrifuged at 1600 g during 10 minutes. Plasma is obtained from the upper phase with a Pasteur pipette.

2.3.1 Wet Plasma

A wet plasma sample is typically processed according to the method of the present invention to generate the ATR-FTIR spectrum shown in FIG. 1 using the following steps:
a) A background is obtained from the empty clean ATR crystal.
b) A blank of water (W) is obtained by measuring the spectrum of 10 microliters of water.

c) 10 microliters of plasma are taken with a micropipette and deposited on the surface of the ATR crystal. Raw spectrum of plasma (RP) is immediately obtained.

d) The final spectrum ($P_w$) of the plasma is obtained subtracting the intensity of the i wavenumber of W to the i wavenumber of RP.

$$P_w(i)=RP(i)-W(i)$$

e) Crystal is cleaned according to the steps set out above.

2.3.2 Dry Plasma

A dry plasma sample is typically processed according to the method of the present invention to generate the ATR-FTIR spectrum shown in FIG. 1 using the following steps:
  a) A background is obtained using the empty clean ATR crystal.
  b) 1 to 5 microlitres (the amount of depending on the application) of plasma are taken with a micropipette and deposited on the surface of the ATR crystal.
  c) Sample is dried through different methods (Allowing to dry/using a drier or heat lamp)
  d) After drying, spectrum ($P_d$) of the plasma is acquired.
  e) Crystal is cleaned according to the General Procedure set out above.

2.4 Red Blood Cells (RBCs) Sample Method

A sample of patient RBCs are obtained by extracting whole blood from the patient in EDTA tubes (or serum tubes if serum is required) or directly with a lancet. WB samples are centrifuged at 1600 g during 10 minutes. RBCs are obtained from the lower phase with a Pasteur pipette.

2.4.1 Wet RBC

A wet RBC sample is typically processed according to the method of the present invention to generate the ATR-FTIR spectrum shown in FIG. 1 using the following steps:
  a) A background is obtained using the empty clean ATR crystal.
  b) A blank of water (W) is obtained by measuring the spectrum of 10 microliters of water.
  c) 10 microliters of RBCs are taken with a micropipette and deposited on the surface of the ATR crystal. Raw spectrum of RBCs (RRBCs) is immediately obtained.
  d) The final spectrum ($RBCs_w$) of the plasma is obtained subtracting the intensity of the i wavenumber of W to the i wavenumber of RP.

$$RBCs_w(i)=RRBCs(i)-W(i)$$

e) Crystal is cleaned according to the General Procedure set out above.

2.4.2 Dry RBC

A dry RBC sample is typically processed according to the method of the present invention to generate the ATR-FTIR spectrum shown in FIG. 1 using the following steps:
  a) A background is obtained using the empty clean ATR crystal.
  b) 1-5 (Depending on the application) microliters of RBCs are taken with a micropipette and deposited on the surface of the ATR crystal.
  c) Sample is dried through different methods (Allowing to dry/using a drier or heat lamp)
  d) After drying, spectrum ($RBCs_d$) of the plasma is obtained.
  e) Crystal is cleaned according to the General Procedure set out above.

2.5 RBC Packed in Solvent

An RBC sample in solvent, such as methonal (MeOH) is typically processed according to the method of the present invention to generate the ATR-FTIR spectrum shown in FIG. 1 using the following steps:
  a) RBC obtained are washed with PBS (phosphate buffered saline), to remove the plasma/serum components and then mixed with 1 mL of cold methanol 0.4:1 (v/v).
  b) 1-5 (Depending on the application) microliters of the RBCs packed in methanol are taken with a micropipette and deposited on the surface of the ATR crystal.
  c) Sample is dried through different methods (Allowing to dry/using a drier or heat lamp)
  d) After drying, spectrum (RBCsm) of the RBC packed in methanol is obtained.
  e) Crystal is cleaned according to the General Procedure set out above.

2.5 Slurry of Coagulated Whole Blood in a Solvent

A slurry of coagulated whole blood in a solvent, such as methanol (MeOH) is typically processed according to the method of the present invention to generate the ATR-FTIR spectrum shown in FIG. 1 using the following steps:
  a) WB is extracted using the same procedure as in section 1.1.
  b) 1-5 microliters of WB are deposited on the ATR crystal with a micropipette.
  c) The same amount of methanol is deposited on the previous drop of WB, creating a slurry of coagulate blood.
  d) Sample is dried through different methods (Allowing to dry/using a drier or heat lamp)
  e) After drying, spectrum of the dry slurry is acquired.
  f) Cleaning of the crystal according to the General Procedure set out above

2.6 Serum/Plasma/Blood Lipid Extracts

Figure 2:
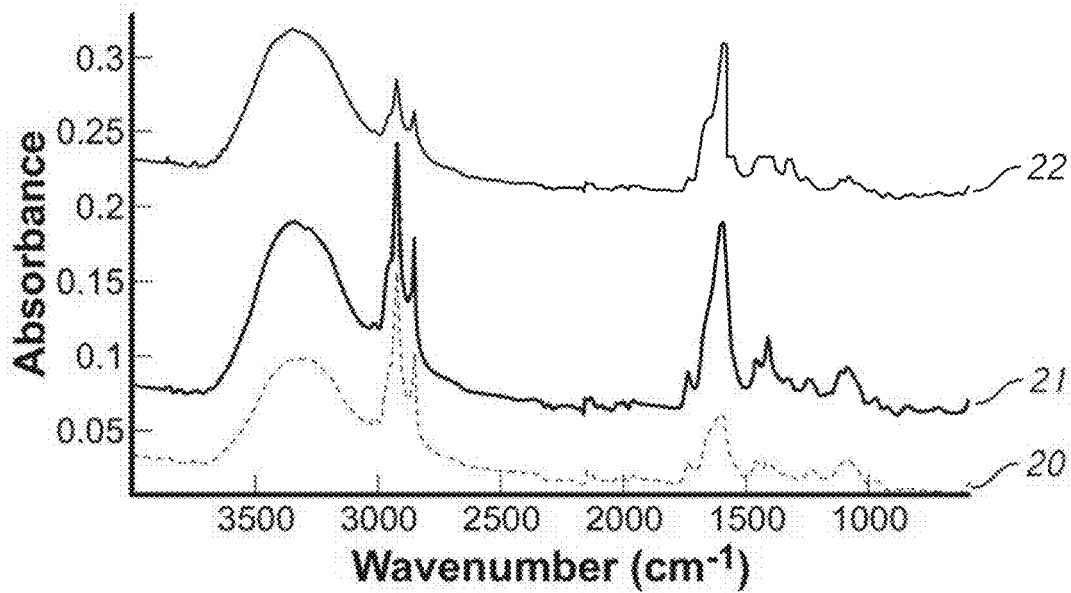
FIG. 2 is an ATR-FTIR spectrum for organic extracts of RBC (20), whole blood (21) and plasma (22) blood lipid extracts.
Figure 3:
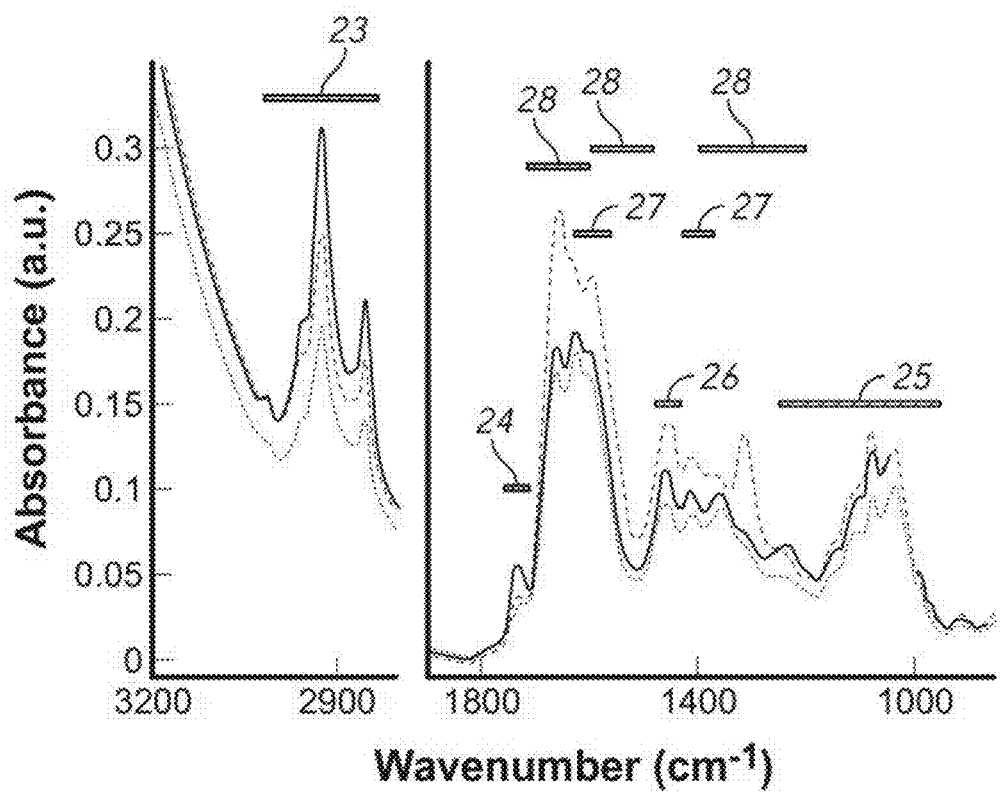
FIG. 3 illustrates typical IR bands associated with biological compounds and their assignments to various moieties in the compounds—$vCH_3$, $vCH_2$, $vCH$, (23); $vCO$ (24); $v(P-O)$, $v(C=O)$ (25); $\delta CH_2$ and $\delta CH_3$ (26); amino acids (27) and amide I, amide II and amide III (28)
Figure 4A:
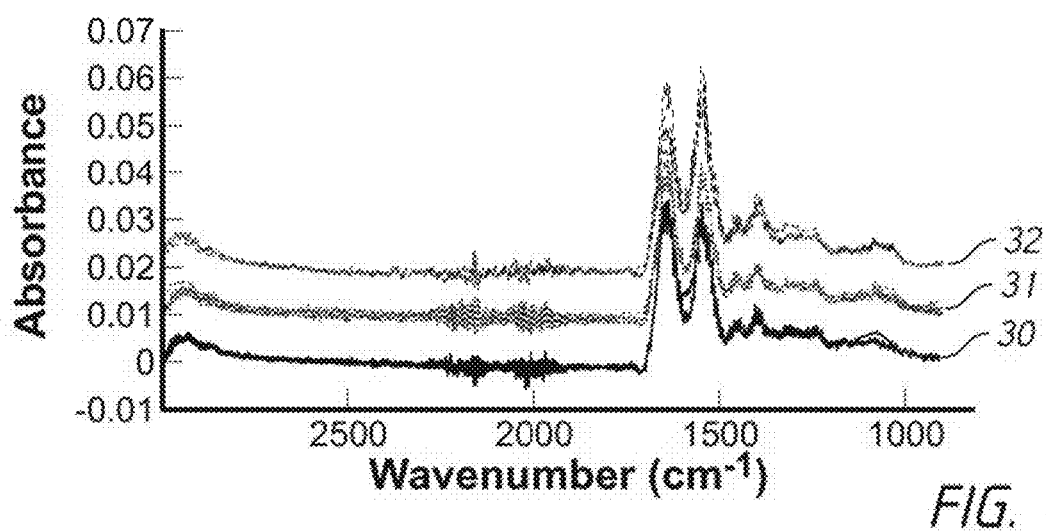
FIG. 4 is an ATR-FTIR spectrum of sera having different loads of Hepatitis B virus (30), Hepatitis C virus (31) and HIV (32), FIG. 4A showing the full spectrum from 3000 to 1000 $cm^{-1}$, FIG. 4B showing an expansion of the region from 1750 to 900 $cm^{-1}$.
FIG. 4C showing an further expansion of the region from 1250 to 950 $cm^{-1}$ which is associated with nucleic acids. A visual inspection shows some bands in the spectra of samples infected by the HIV around 970 and 1160 $cm^{-1}$. Those bands (black arrows), do not appear in the spectra obtained from Hepatitis infected patients, and can be related to the presence of RNA and DNA.
Figure 4B:
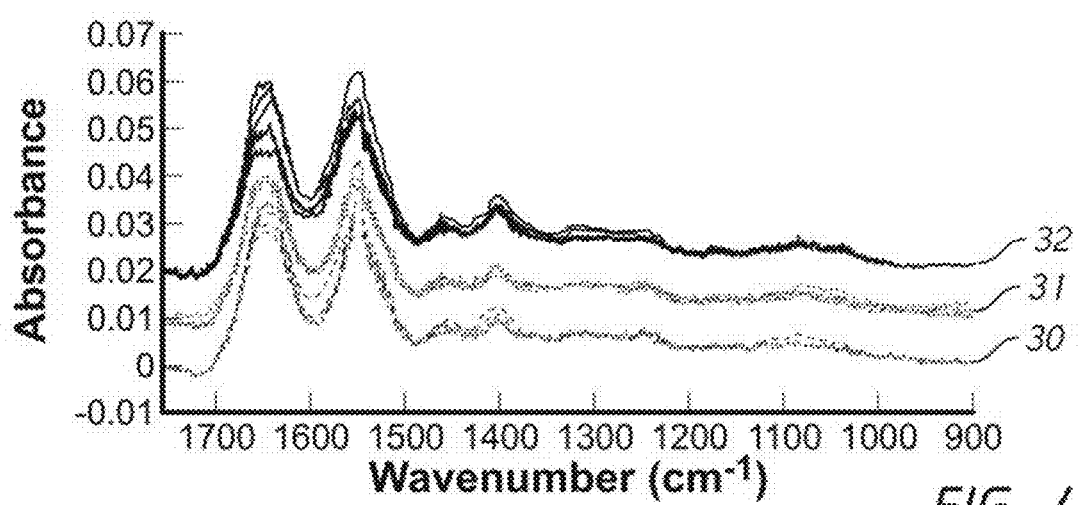
Figure 4C:
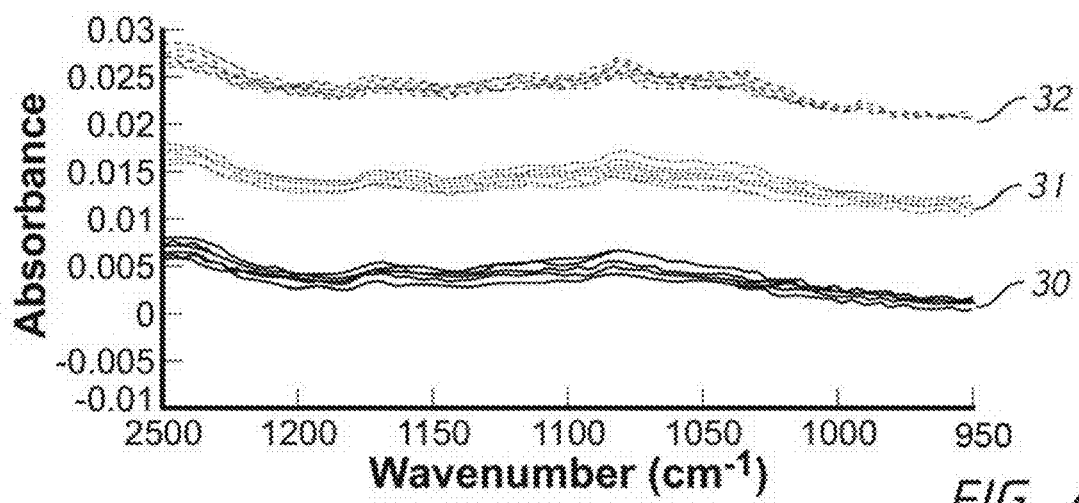
Figure 5A:
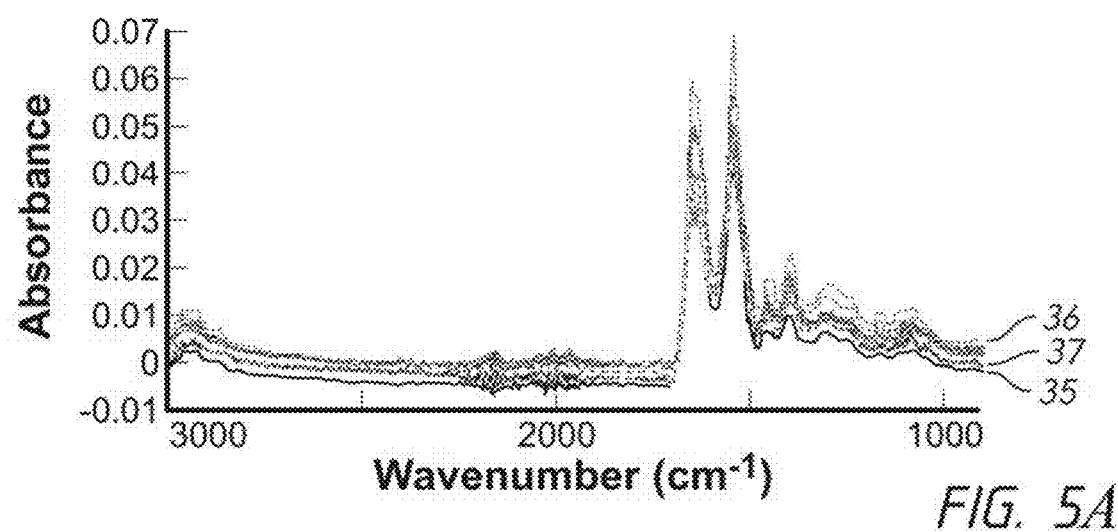
FIG. 5A shows the full spectrum from 3000 to 1000 $cm^{-1}$.
Figure 5B:
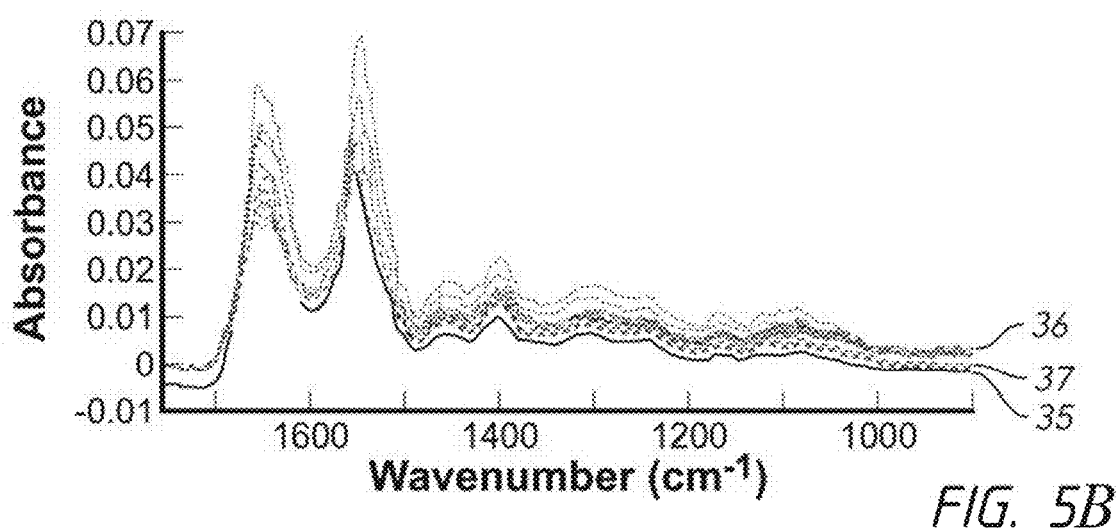
FIG. 5B shows an expansion of the region from 1750 to 900 $cm^{-1}$.
Figure 5C:
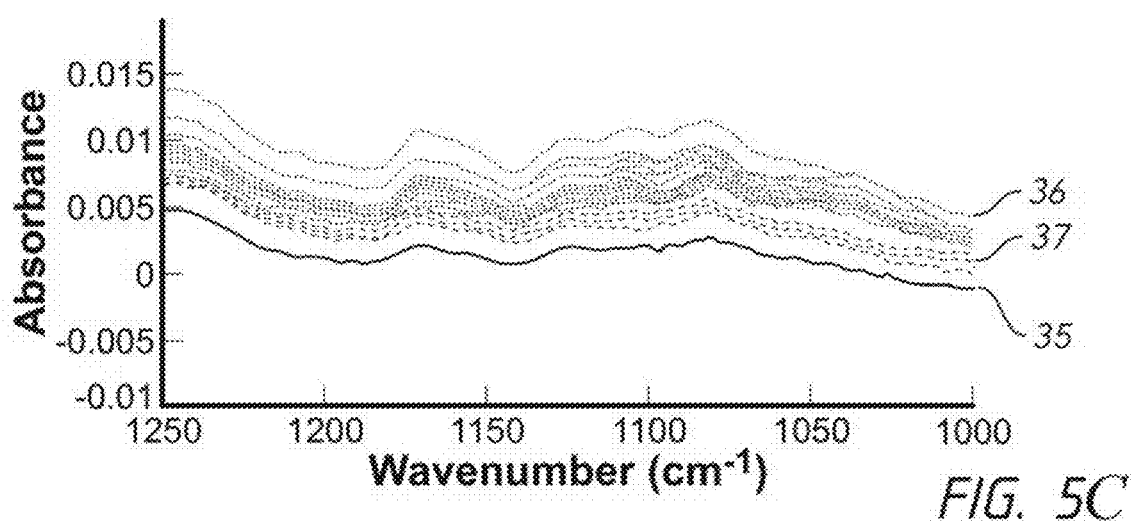
FIG. 5C shows a further expansion of the region from 1250 to 950 $cm^{-1}$ which is associated with nucleic acids. In this case the bands at the HIV spectra observed around 1140 and 1110 $cm^{-1}$ are even more obvious.
Figure 6A:
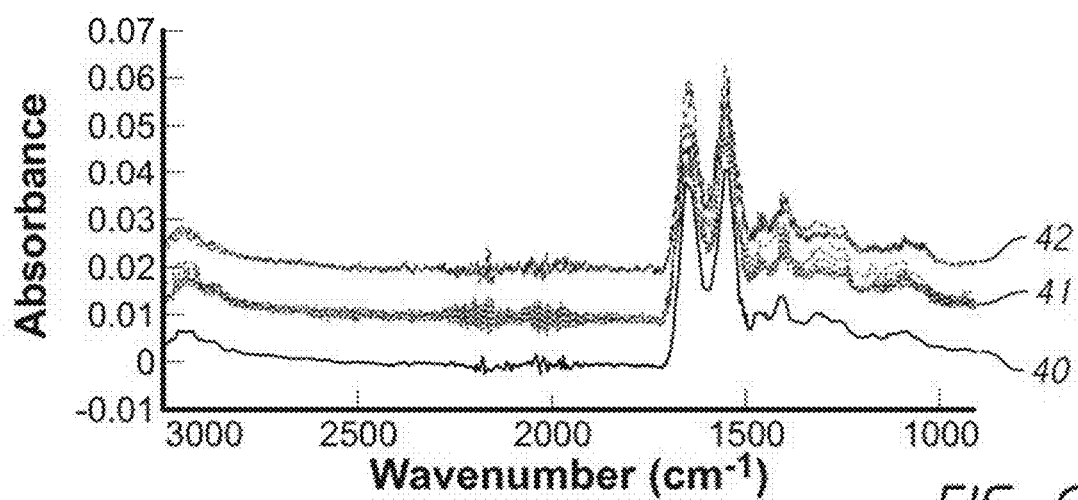
FIG. 6A shows the full spectrum from 3000 to 1000 $cm^{-1}$.
Figure 6B:
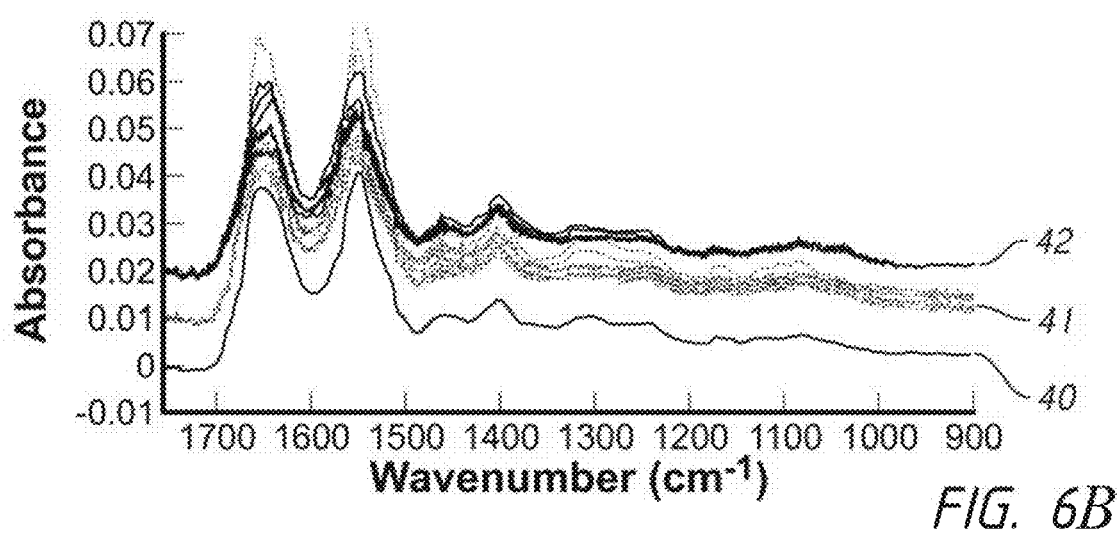
FIG. 6B shows an expansion of the region from 1750 to 900 $cm^{-1}$.
Figure 6C:
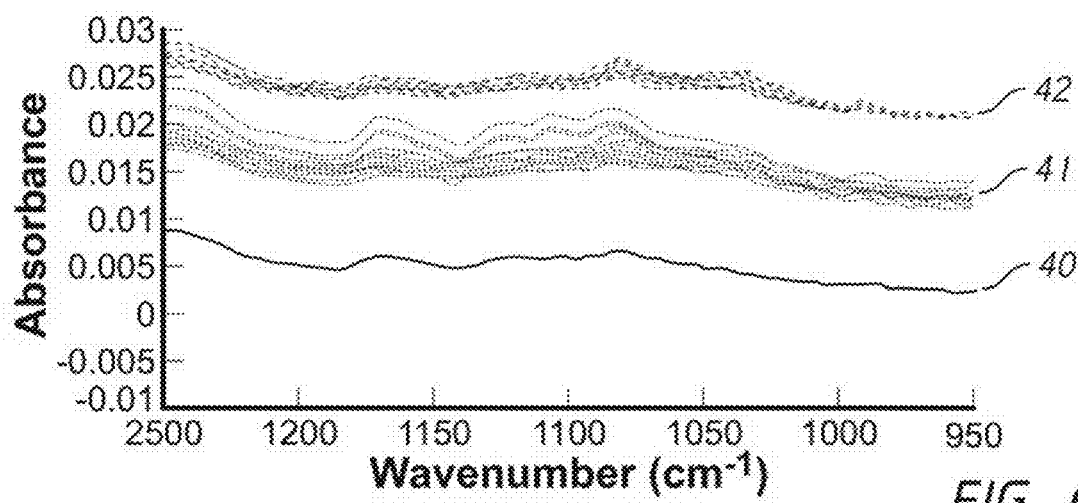
FIG. 6C shows a further expansion of the region from 1250 to 950 $cm^{-1}$ which is associated with nucleic acids. Again, the bands specifically assigned to nucleic are shown, being much more intense in the case of the WB. IT may be caused by the presence of lymphocytes in the WB. Those bands are not found in the control under study.
Figure 7A:
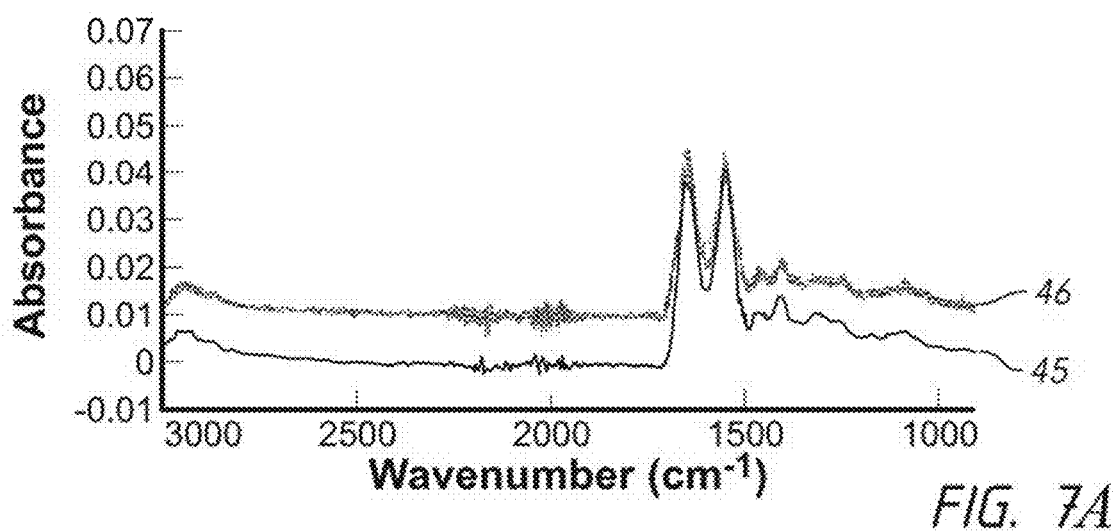
FIG. 7A shows the full spectrum from 3000 to 1000 $cm^{-1}$.
Figure 7B:
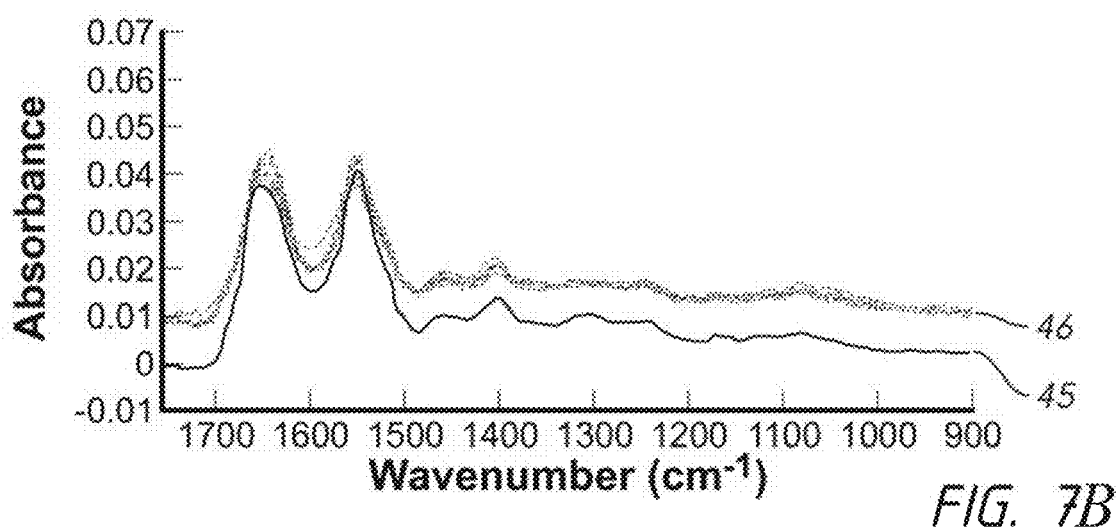
FIG. 7B shows an expansion of the region from 1750 to 900 $cm^{-1}$.
Figure 7C:
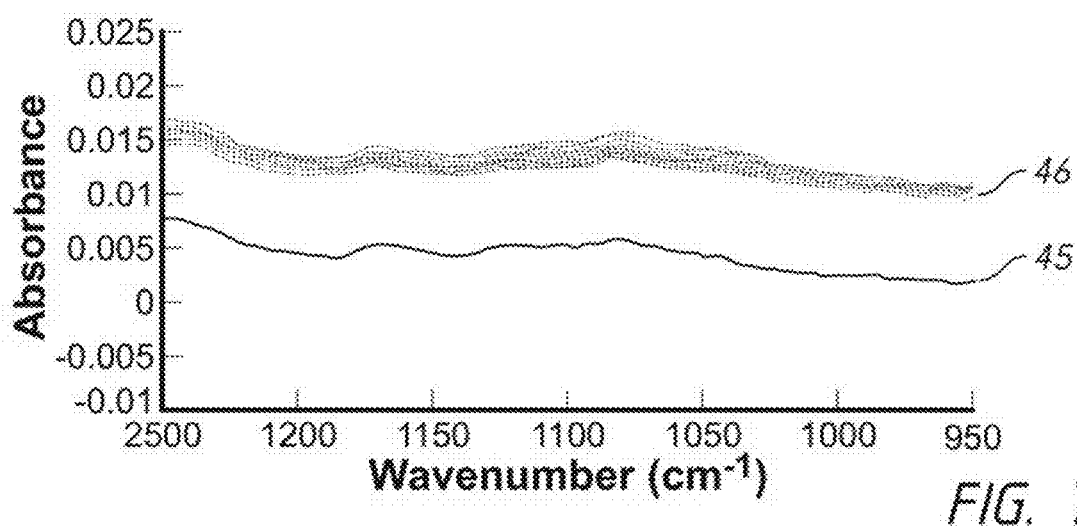
FIG. 7C shows a further expansion of the region from 1250 to 950 $cm^{-1}$ which is associated with nucleic acids. Naked eye cannot found differences between the spectra of the control (45) and the pathological samples of hepatitis B virus (46).
Figure 8A:
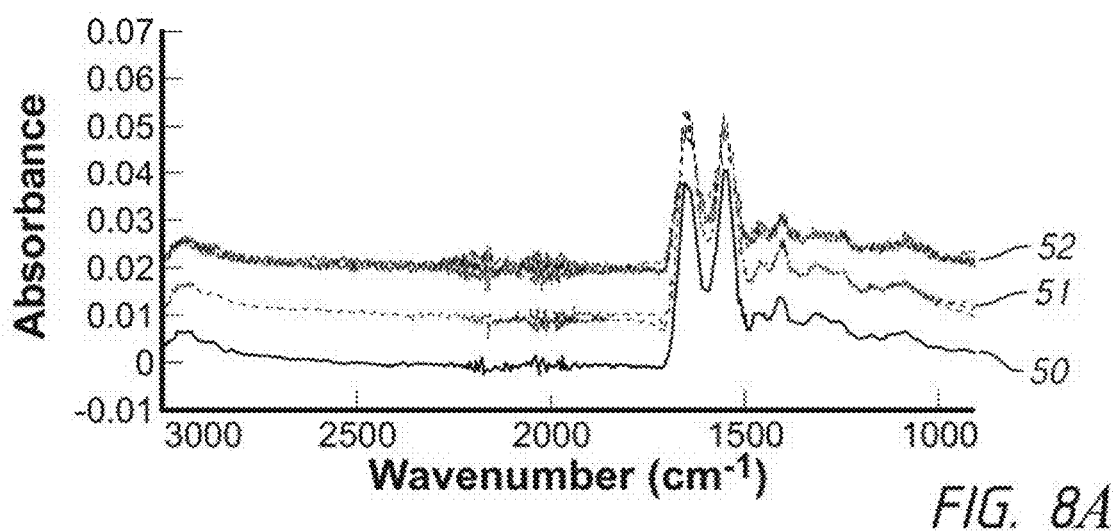
FIG. 8A shows the full spectrum from 3000 to 1000 $cm^{-1}$.
Figure 8B:
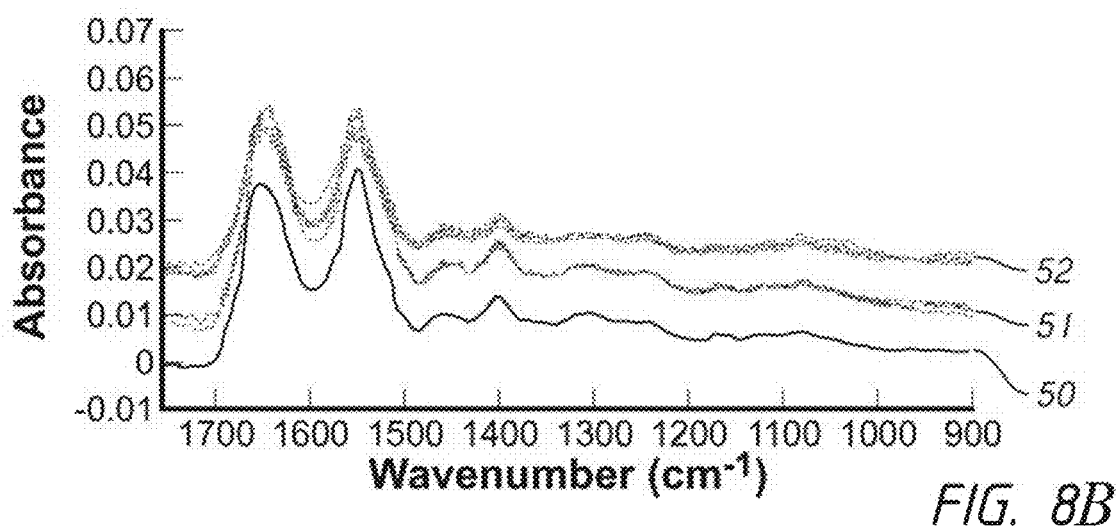
FIG. 8B shows an expansion of the region from 1750 to 900 $cm^{-1}$.
Figure 8C:
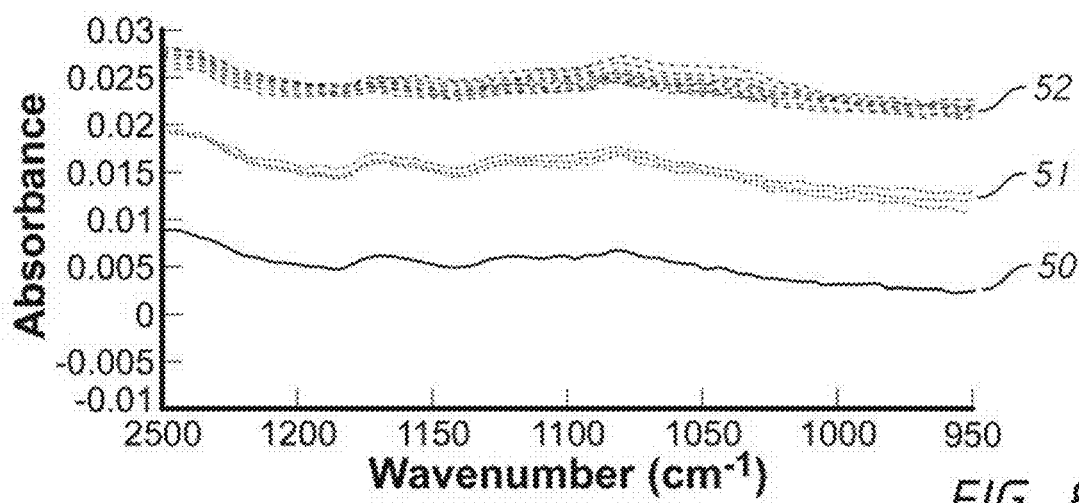
FIG. 8C shows a further expansion of the region from 1250 to 950 cm$^{-1}$ which is associated with nucleic acids. Again, naked eye cannot found differences between the spectra of the control (50) and the pathological samples of hepatitis C in whole blood (51) and serum (52).
Figure 9A:
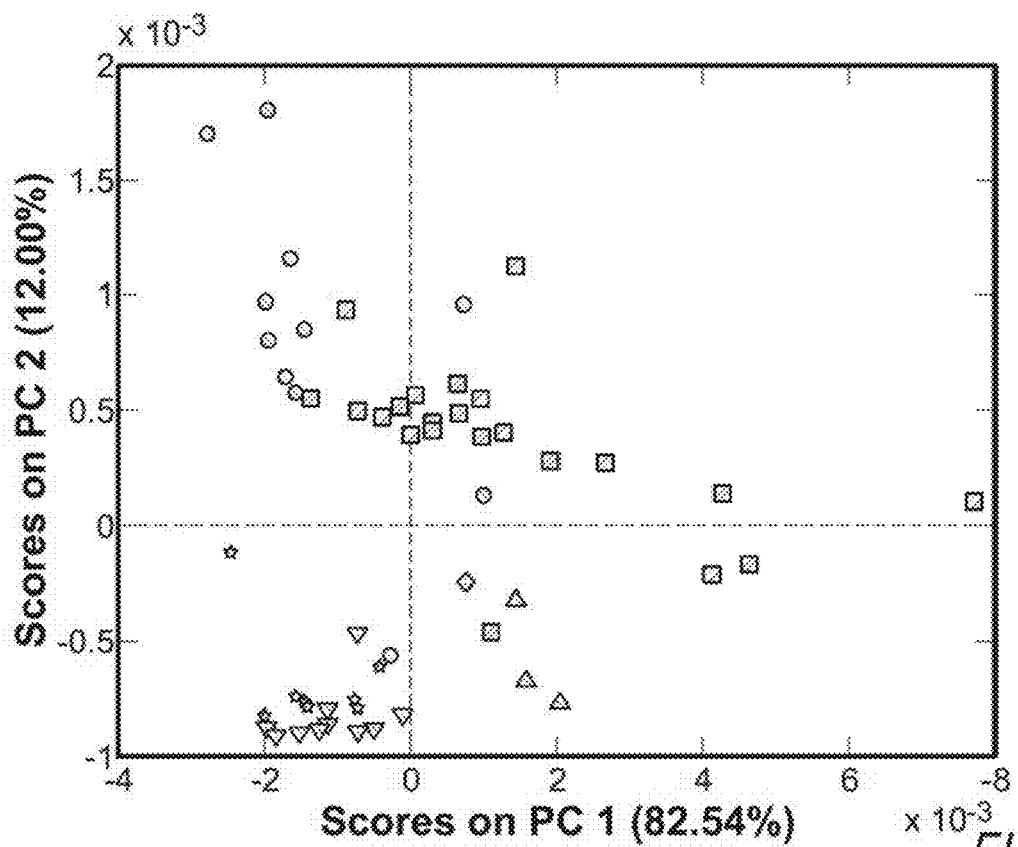
Figure 9B:
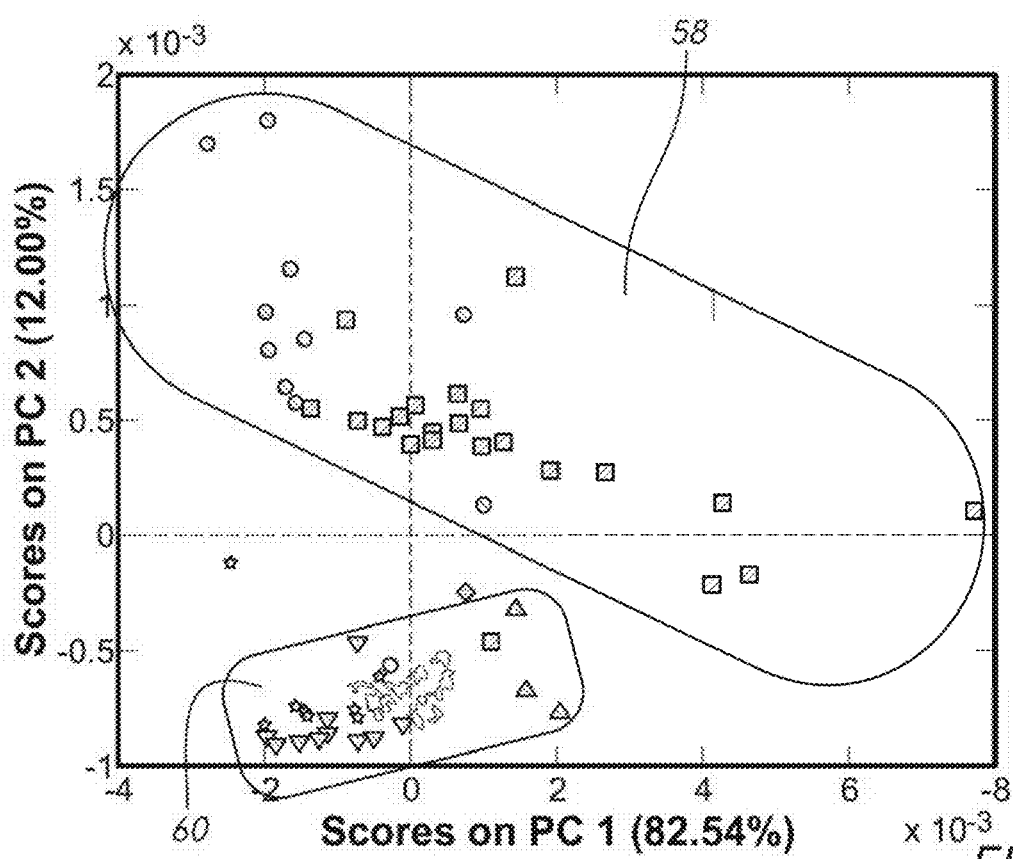
Figure 10A:
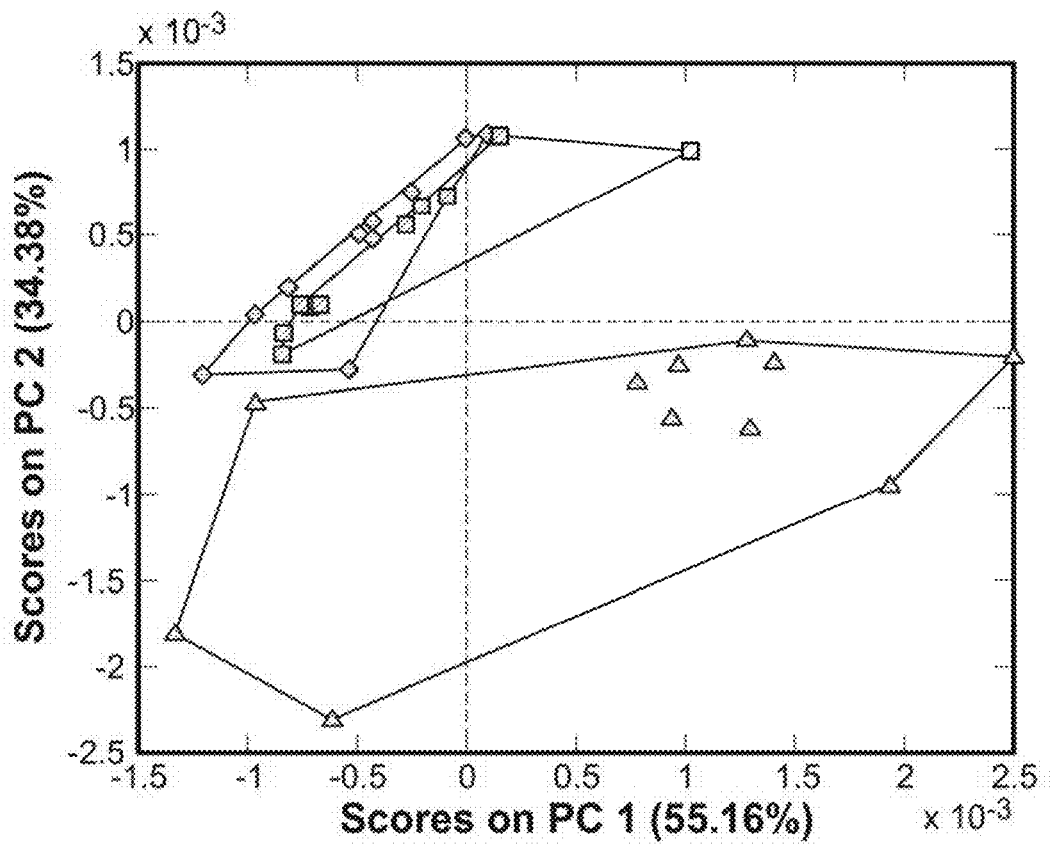
FIG. 10 is a multivariate analysis of the serum spectra in two different formats (FIG. 10A and FIG. 10B) for Hepatitis B (◇), Hepatitis C (□) and HIV (▲). In the case of serum data, HIV-HIV and hepatitis are clearly separated in the PC1 (62) vs PC2 space (63).
Figure 10B:
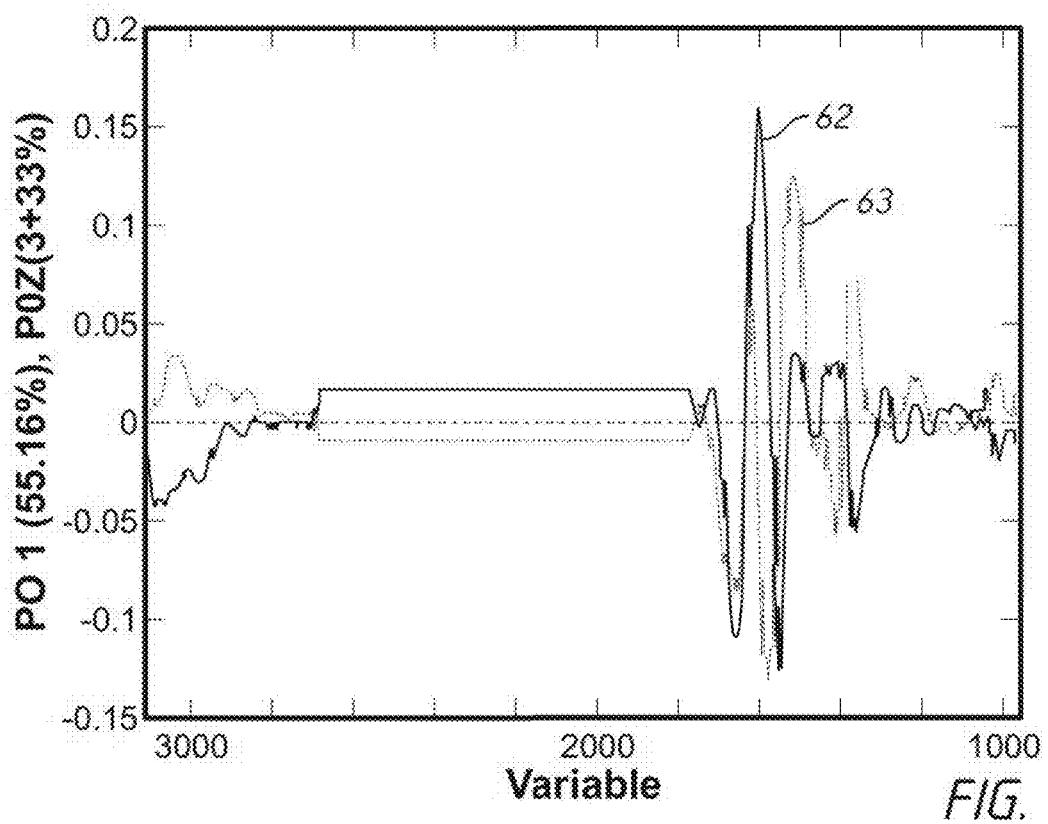
Figure 11A:
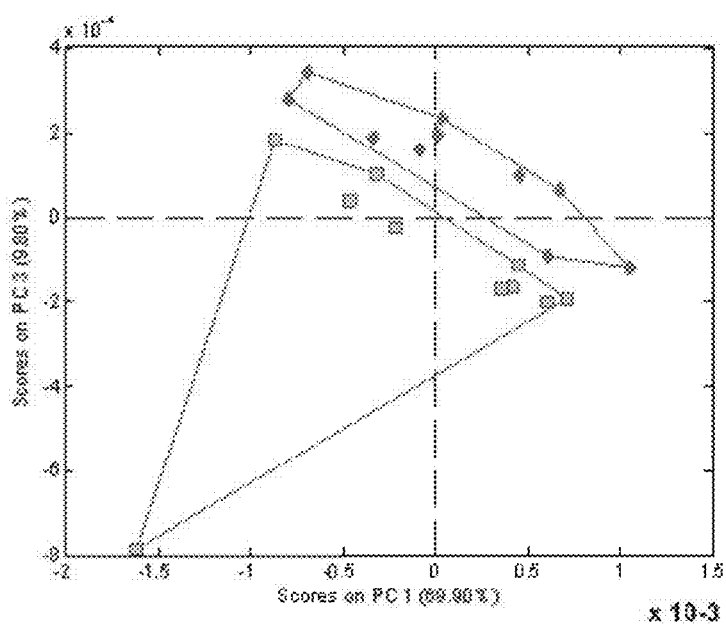
FIG. 11 is a multivariate analysis of the serum spectra (hepatitis only) in two different formats (FIG. 11A and FIG. 11B). Although the visual inspection of the spectra did not reveal differences, in the comparison between the Hepatitis B (◇) and Hepatitis C (□) on the scores plot, there are different clusters for each illness.
Figure 11B:
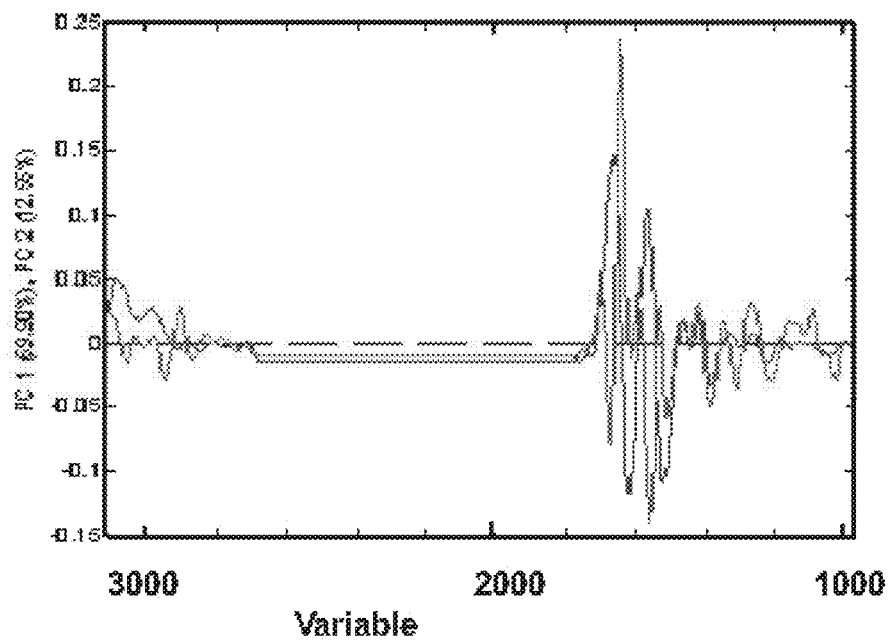
Figure 12:
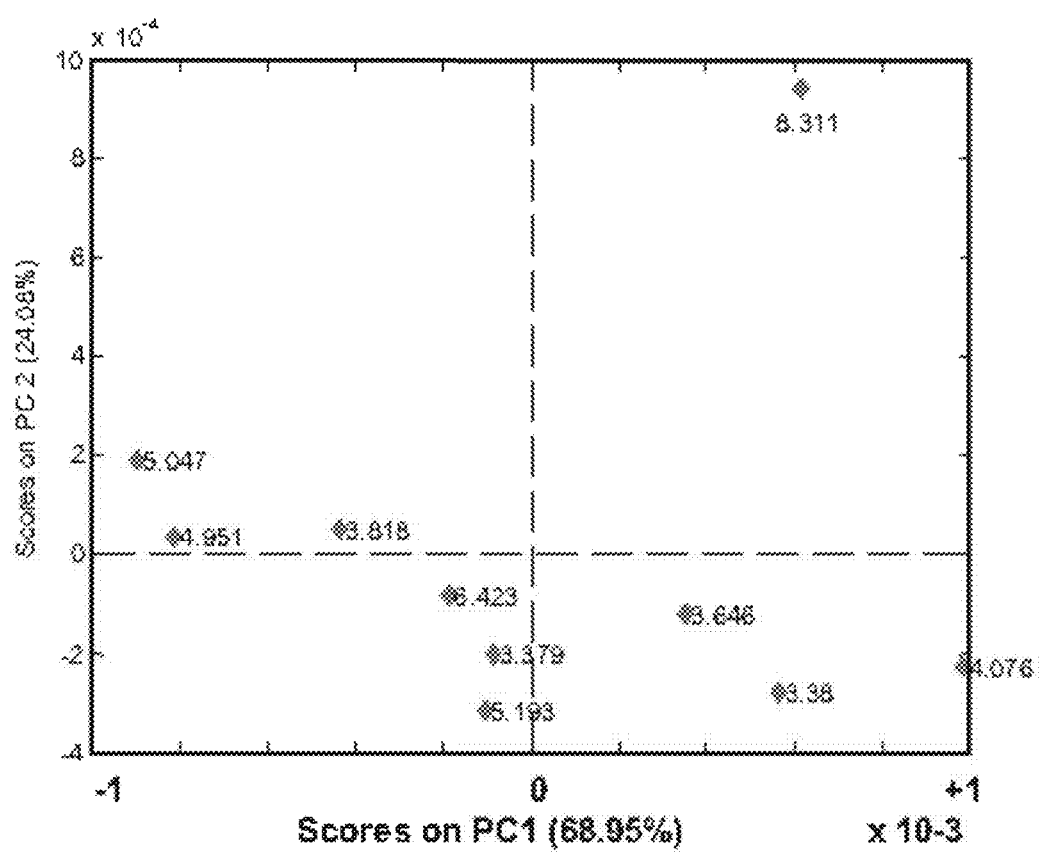
FIG. 12 is a multivariate analysis of the serum spectra (hepatitis B only)(◇). Labels indicate the log of the virus load. The sample with the highest load is clearly separated from the others.
Figure 13A:
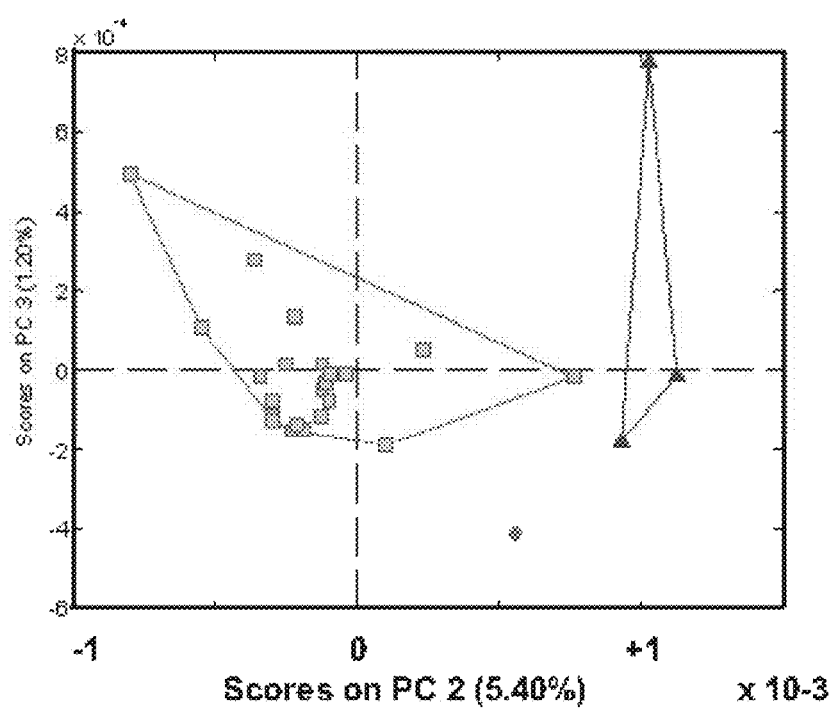
FIG. 13 is a multivariate analysis of the whole blood spectra in two different formats (FIG. 13A and FIG. 13B). In the case of whole blood, the scores PC2 (70) and PC3 (71) clearly separate among the HIV (□), hepatitis C (▲) and the control (◇).
Figure 13B:
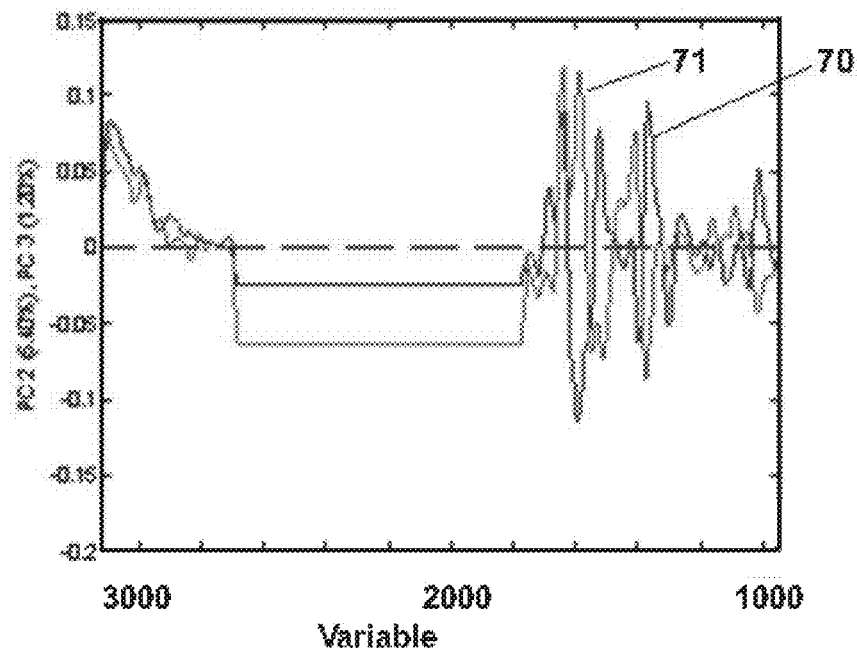
Figure 14A:
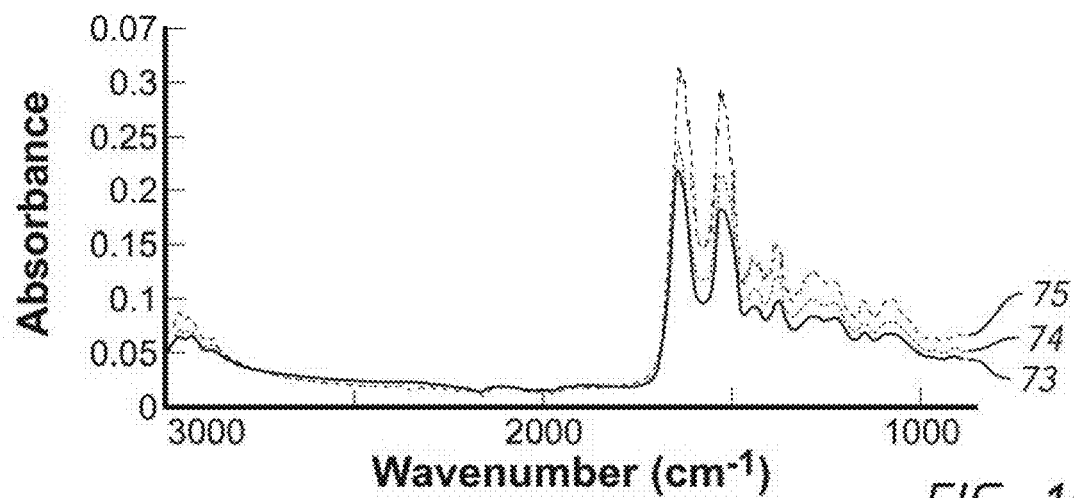
FIG. 14A shows the full spectrum from 3000 to 1000 cm$^{-1}$.
Figure 14B:
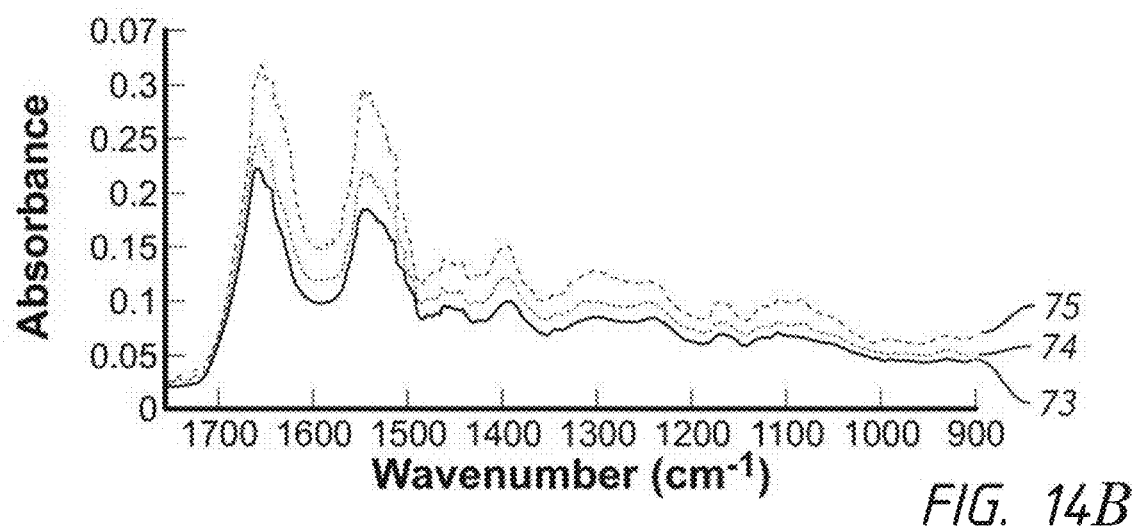
FIG. 14B shows an expansion of the region from 1750 to 900 cm$^{-1}$ and FIG. 14C shows a further expansion of the region from 1250 to 950 cm$^{-1}$ which is associated with nucleic acids.
Figure 14C:
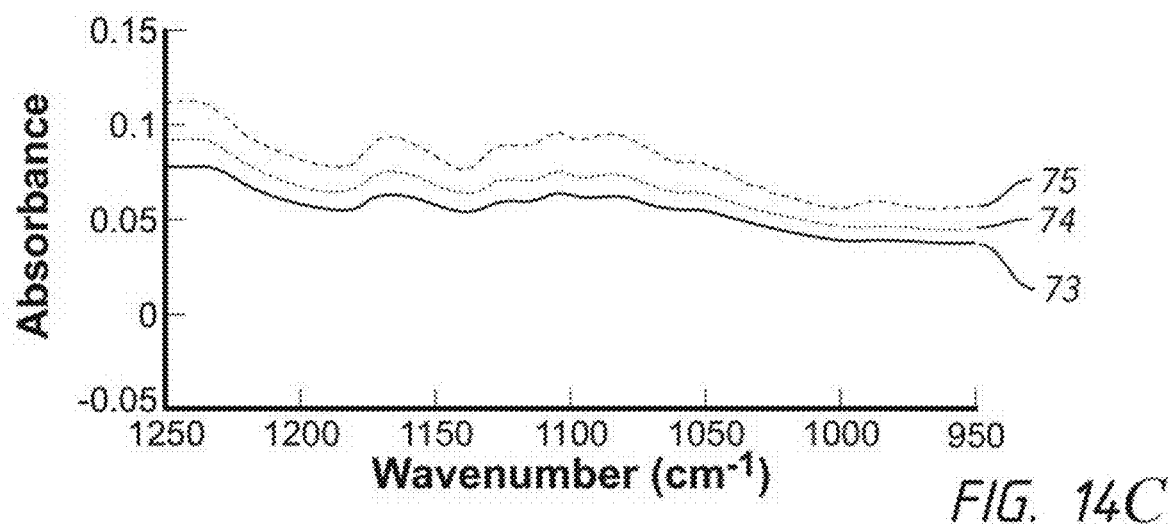
Figure 15A:
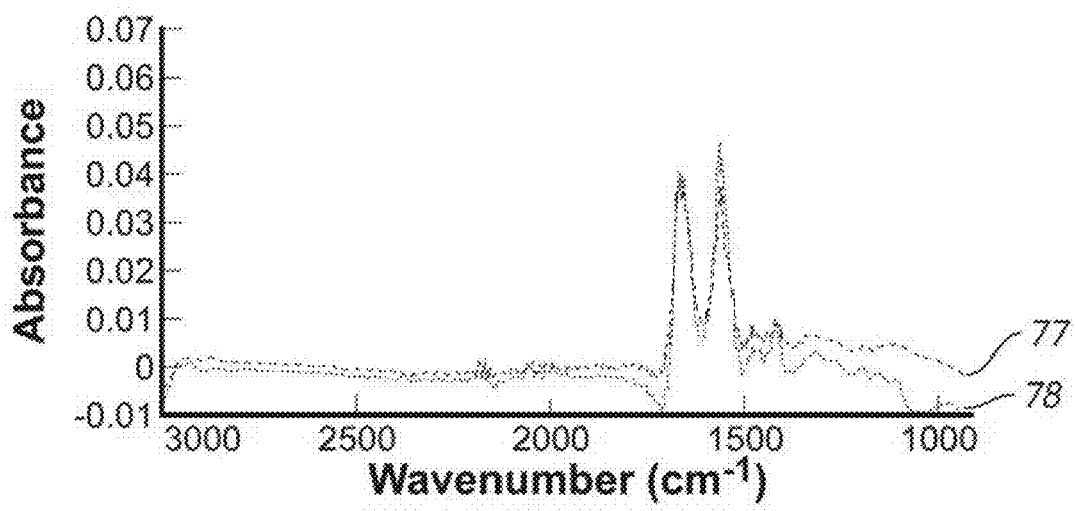
FIG. 15A shows the full spectrum from 3000 to 1000 cm$^{-1}$.
Figure 15B:
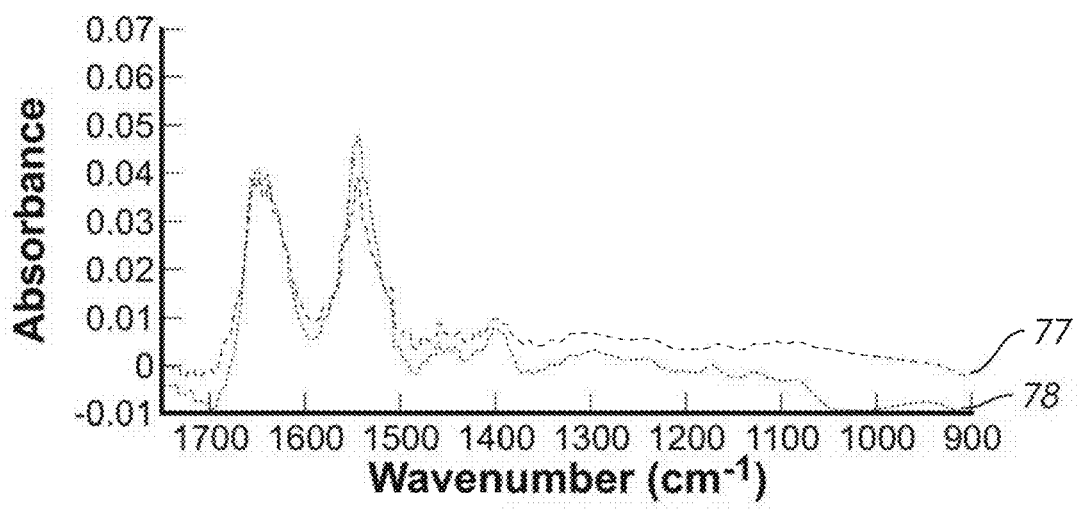
FIG. 15B shows an expansion of the region from 1750 to 900 cm$^{-1}$.
Figure 16A:
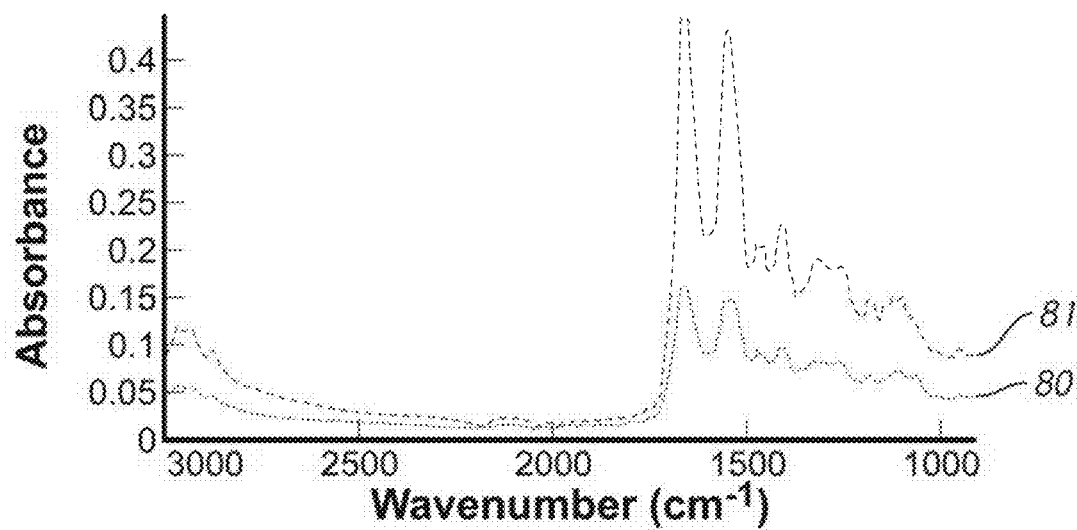
FIG. 16A shows the full spectrum from 3000 to 1000 cm$^{-1}$.
Figure 16B:
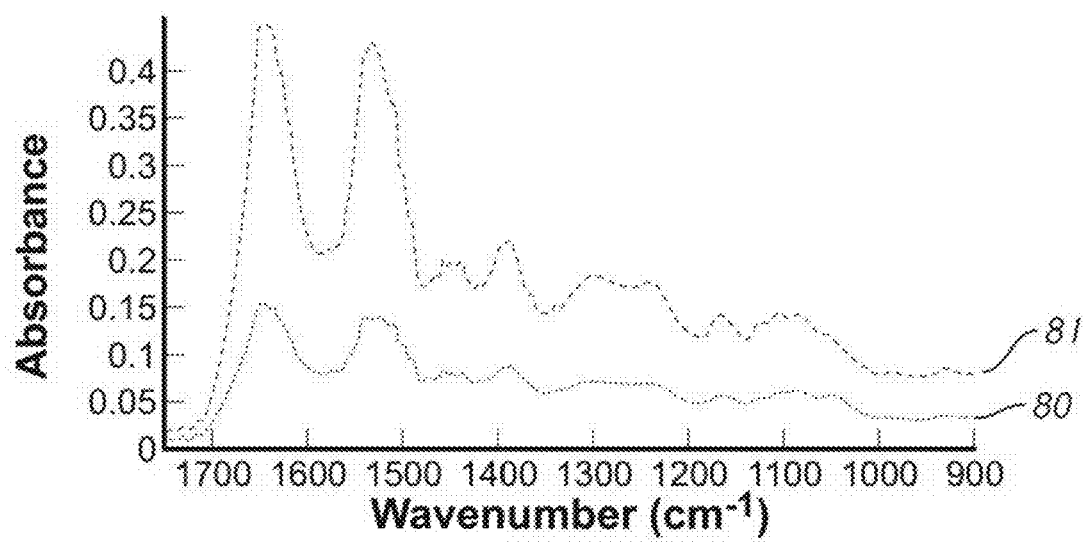
FIG. 16B shows an expansion of the region from 1750 to 900 cm$^{-1}$.
Figure 17:
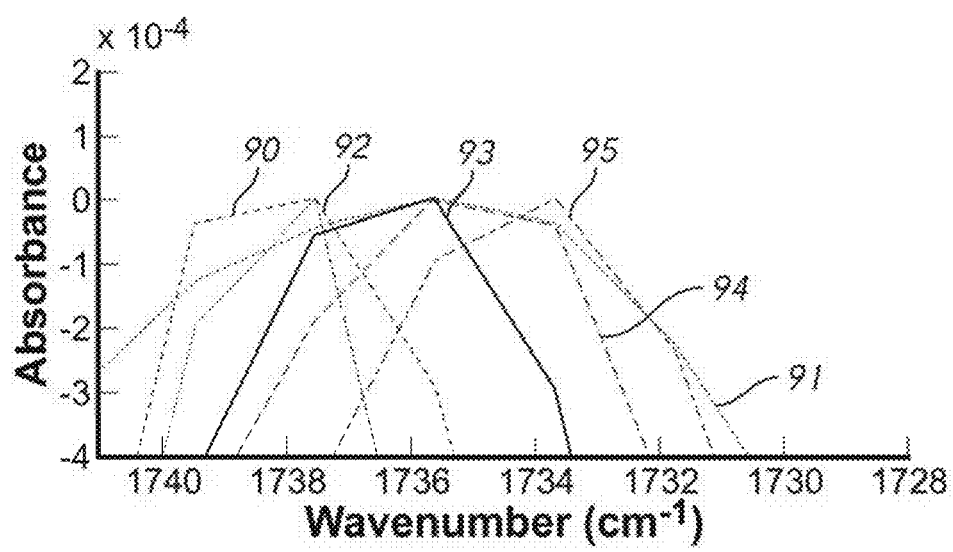
FIG. 17 includes ATR-FTIR plots of methanol extracts of WB spiked with different loadings of malaria (control (90); 0.0077% (91): 0.031% (92); 0.25% (93); 0.49% (94); 1.96% (95).
Figure 18:
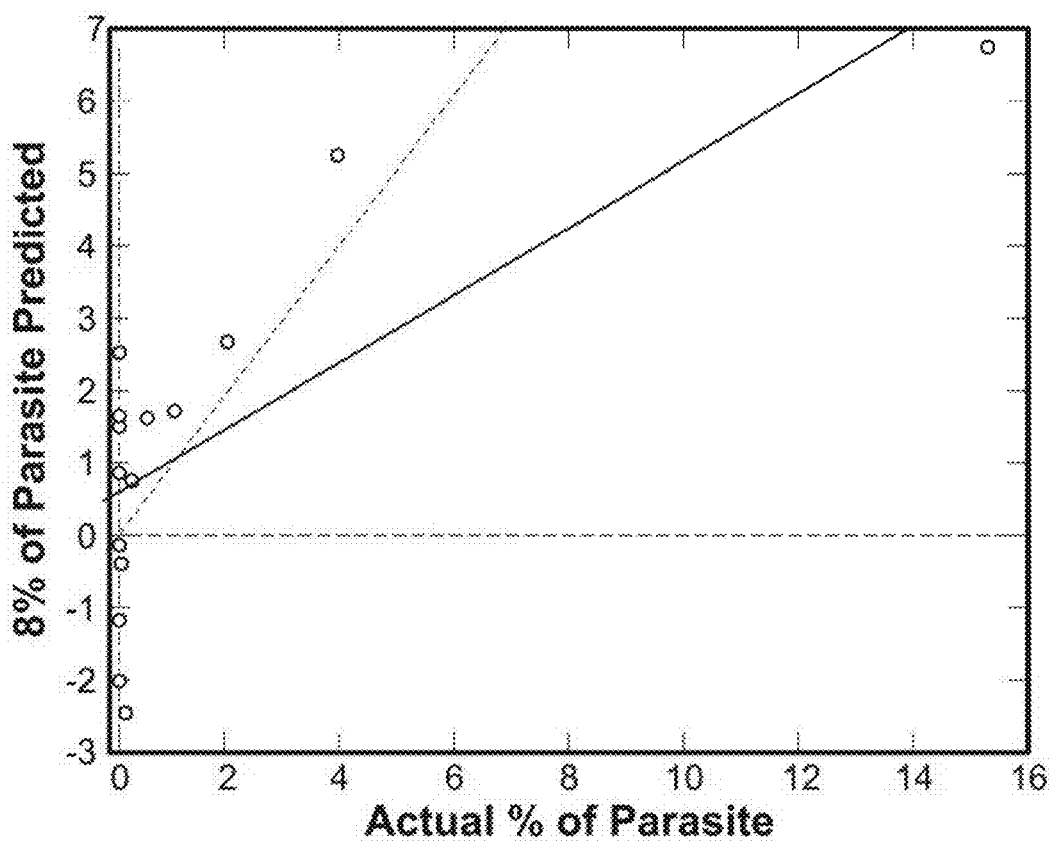
FIG. 18 is a partial least squares regression plot of predicted vs actual level of parasite in the WB samples. The regression analysis enables discrimination between high and low parasite loadings. Note that the method is linear, and covers several orders of magnitude. A permutation test indicated that the regression is significant at the 95% confidence level.
Figure 19:
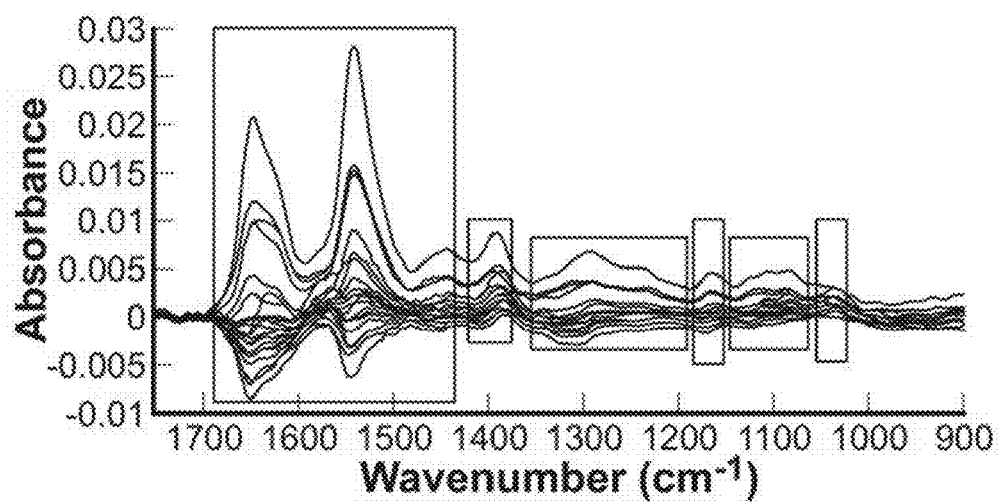
FIG. 19 is an ATR-FTIR spectrum of whole blood samples having a high viral load of HIV after subtraction of a control spectra.
Figure 20:
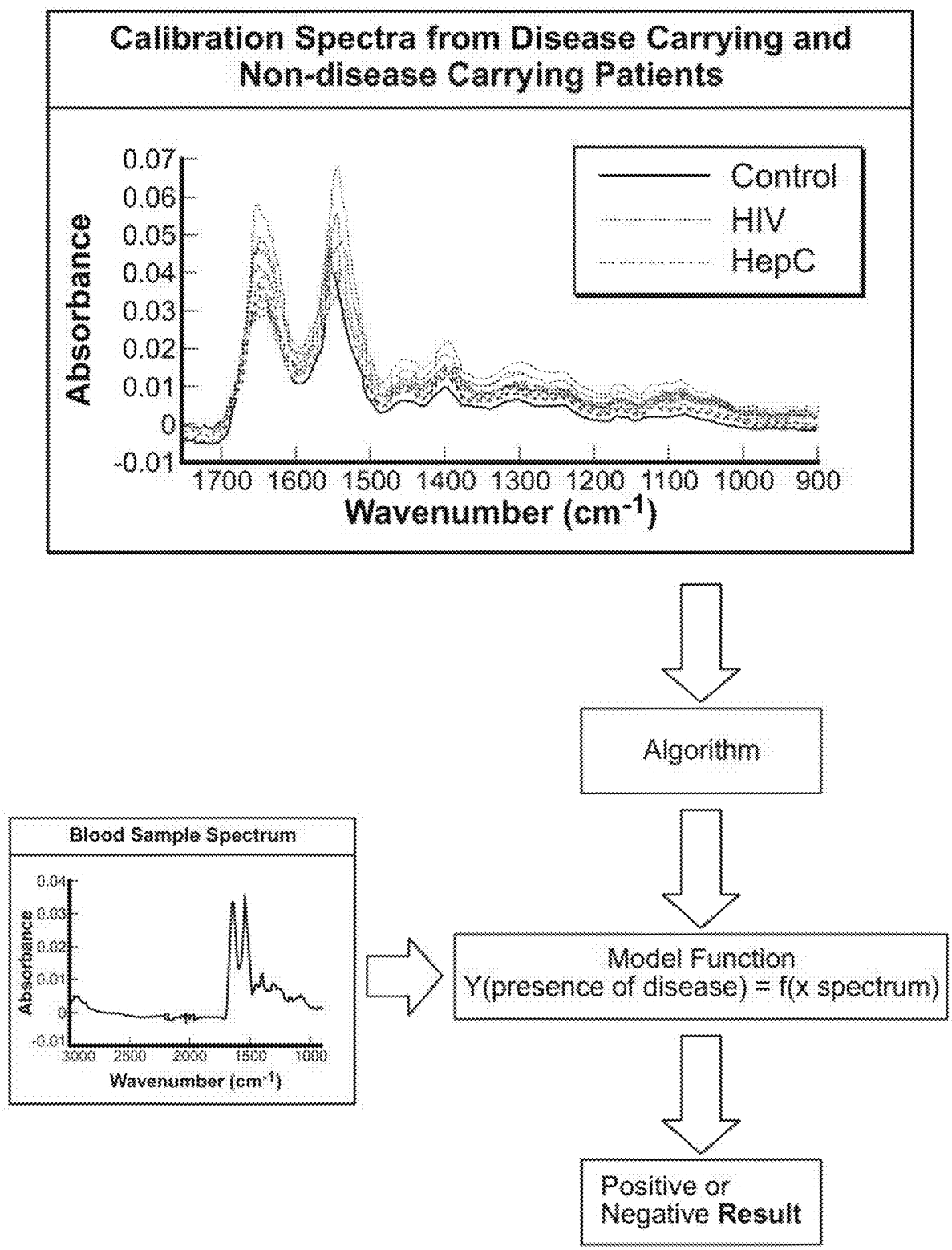
FIG. 20 is a flow chart illustrating the steps according to one embodiment of the method of the present invention.
Figure 21:
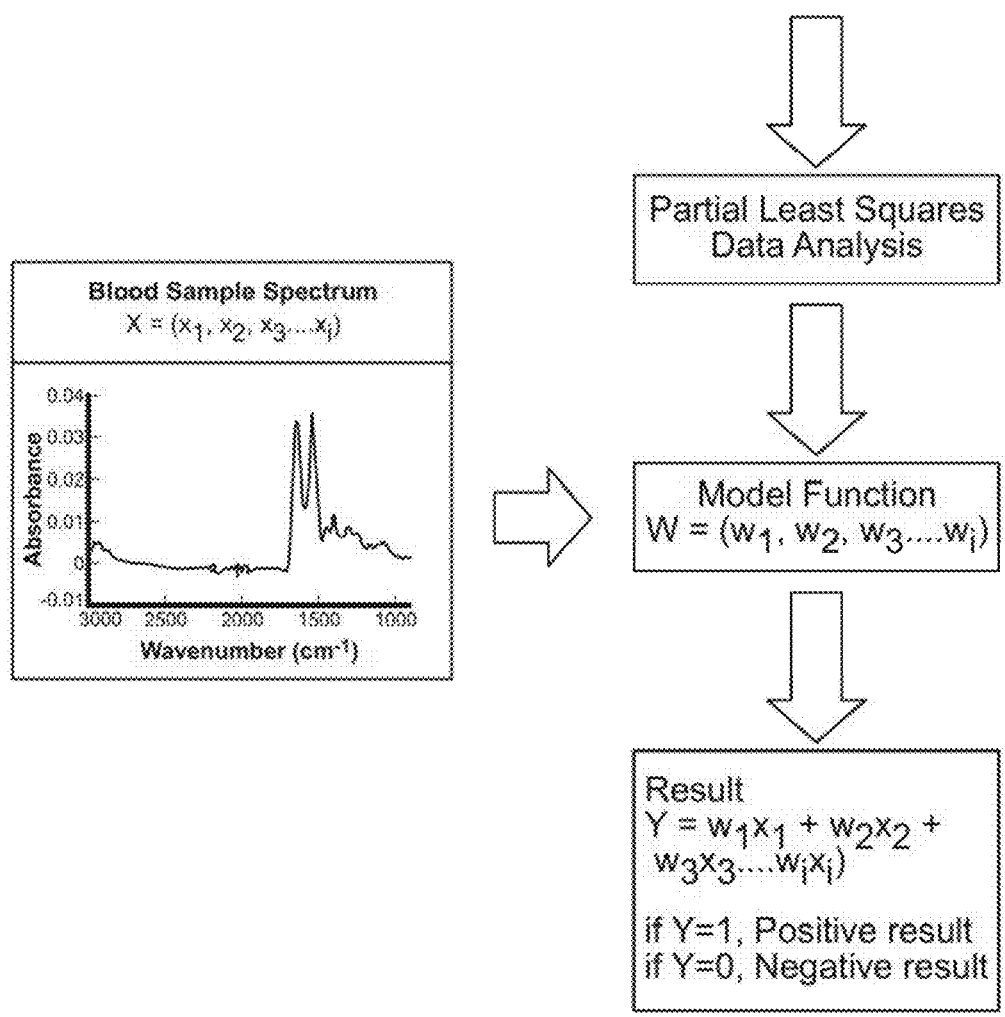
FIG. 21 is a flow chart illustrating in more detail the steps of FIG. 20, including an indication of the preferred data manipulation.
Figure 22:
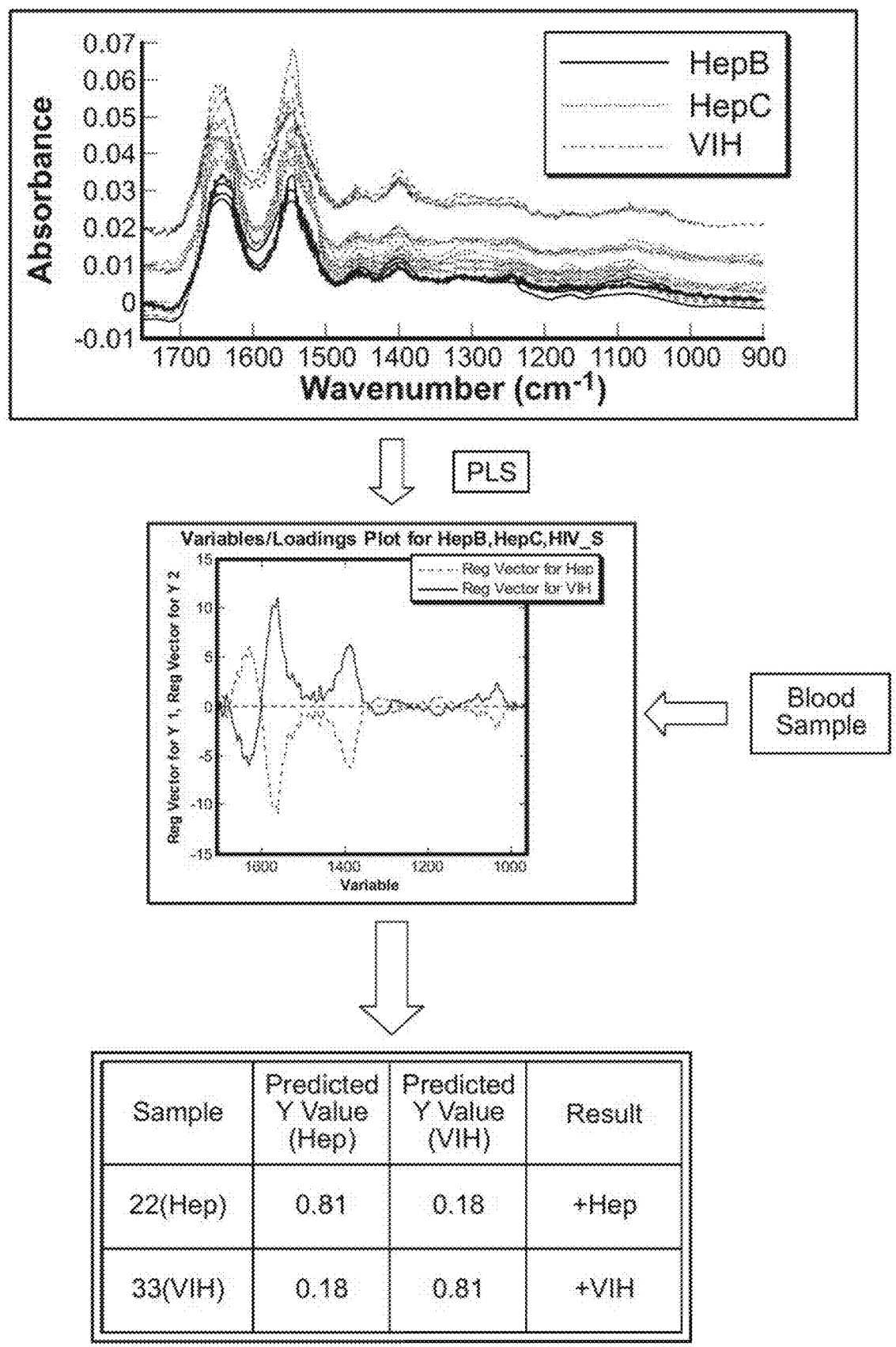
FIG. 22 is a flow chart illustrating the method of the present invention when used to create a model for classifying blood samples as positive or negative for hepatitis virus (Hep) or HIV.
Figure 23:
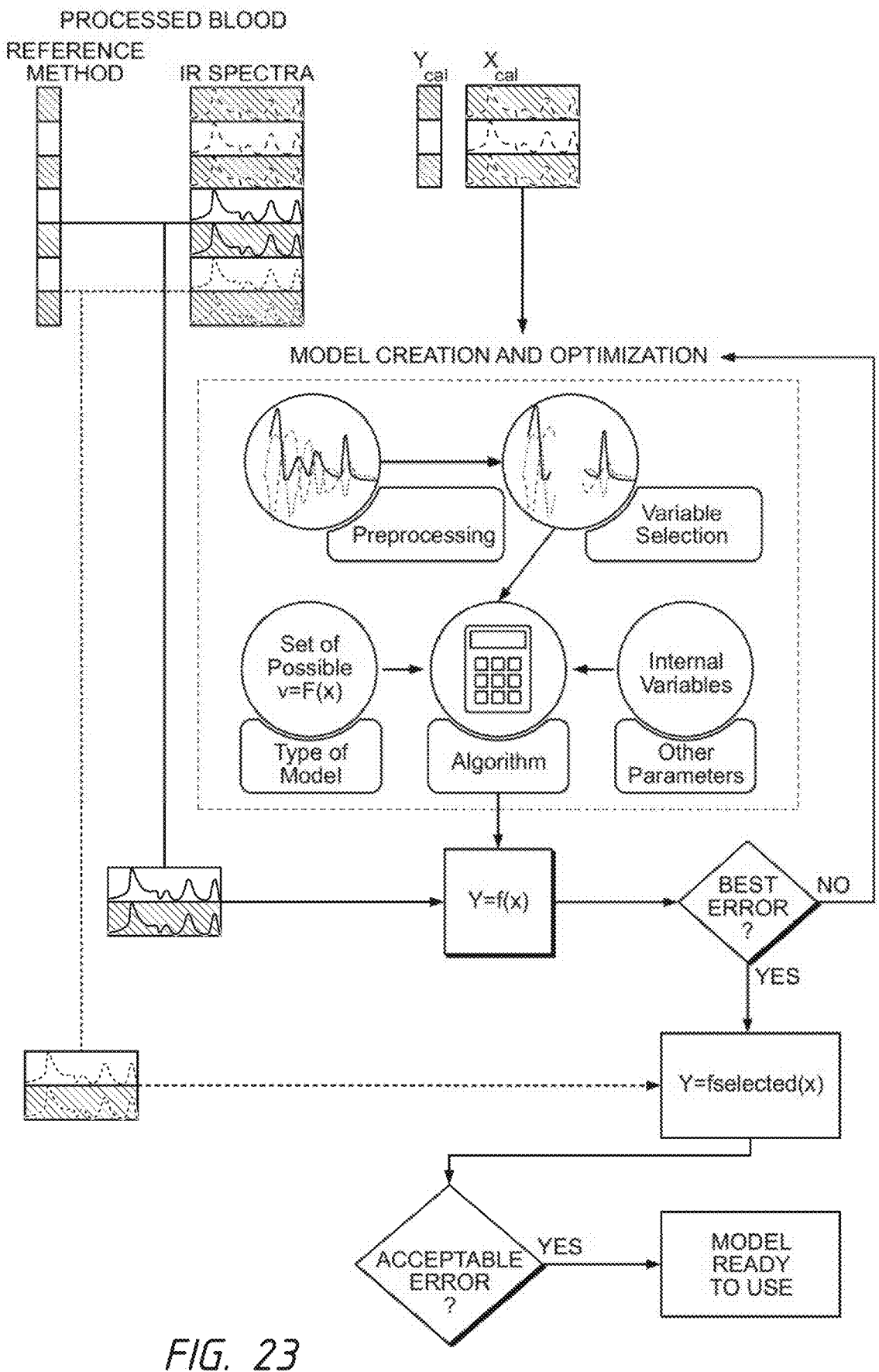
FIG. 23 is a further flow chart depicting the creation of a suitable mode for classifying blood samples according to the present invention.
Figure 24:
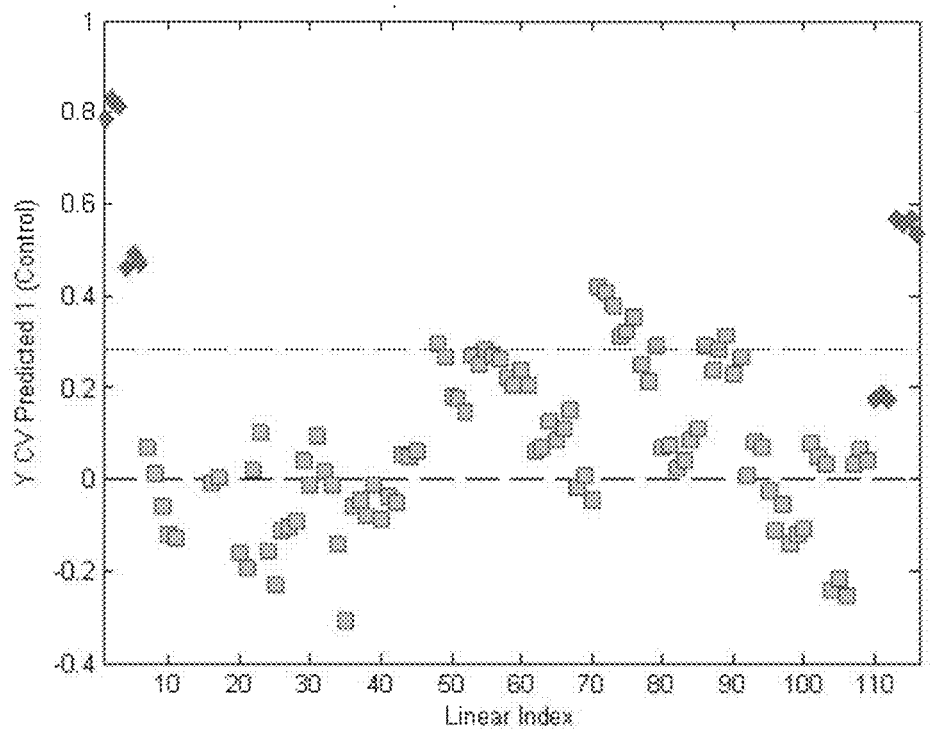
FIG. 24 is a plot of Y CV predicted against a linear index for methanol fixed RBC blood samples infected with malaria (□) and control (◇) samples with Discrim Y 1 marked in broken line.
Figure 25:
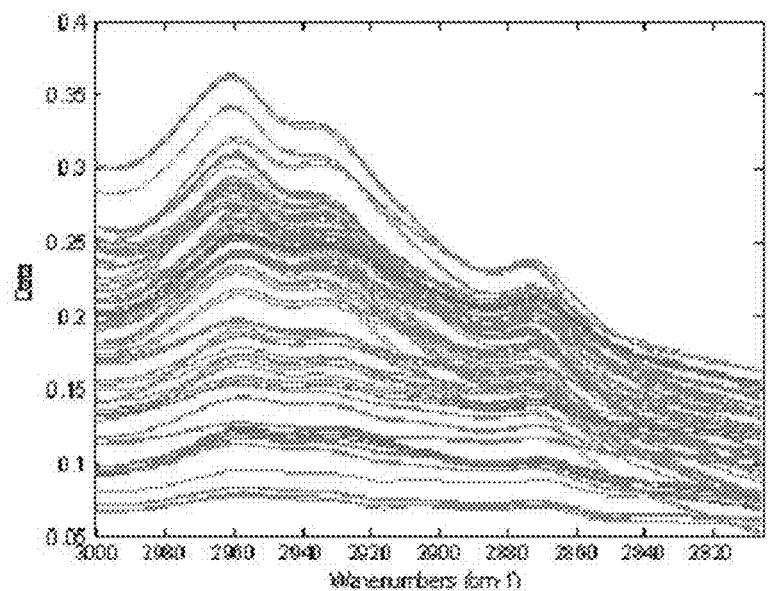
FIG. 25 is an IR absorption plot for the spectral window from 3000-2820 cm$^{-1}$.
Figure 26:
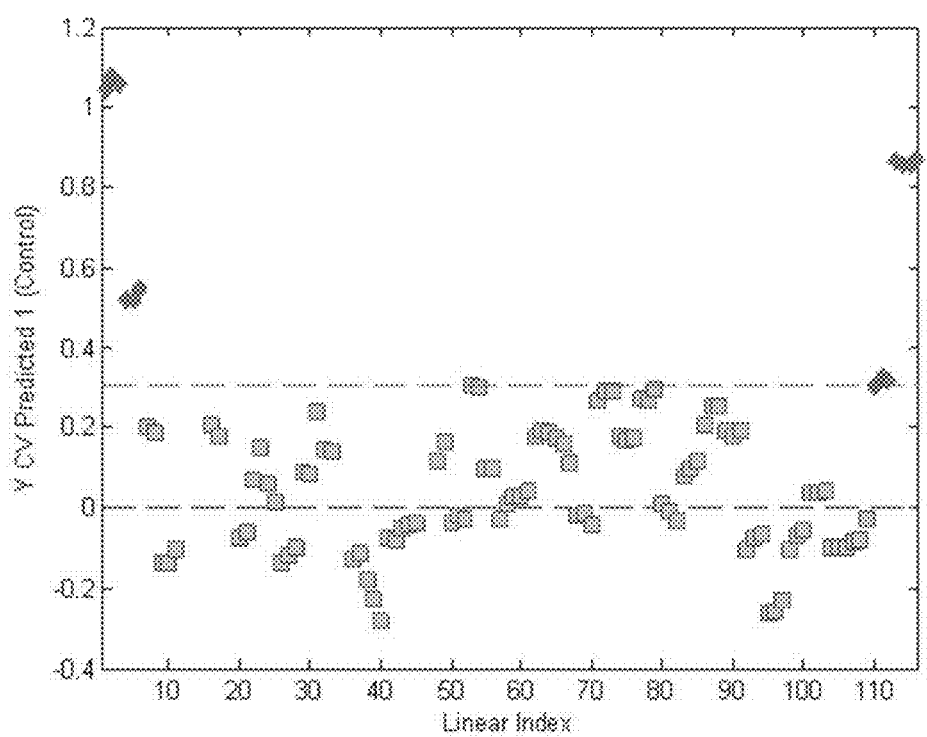
FIG. 26 is a plot of Y CV predicted against a linear index for methanol fixed RBC blood samples infected with malaria (□) and control (◇) samples.
Figure 27:
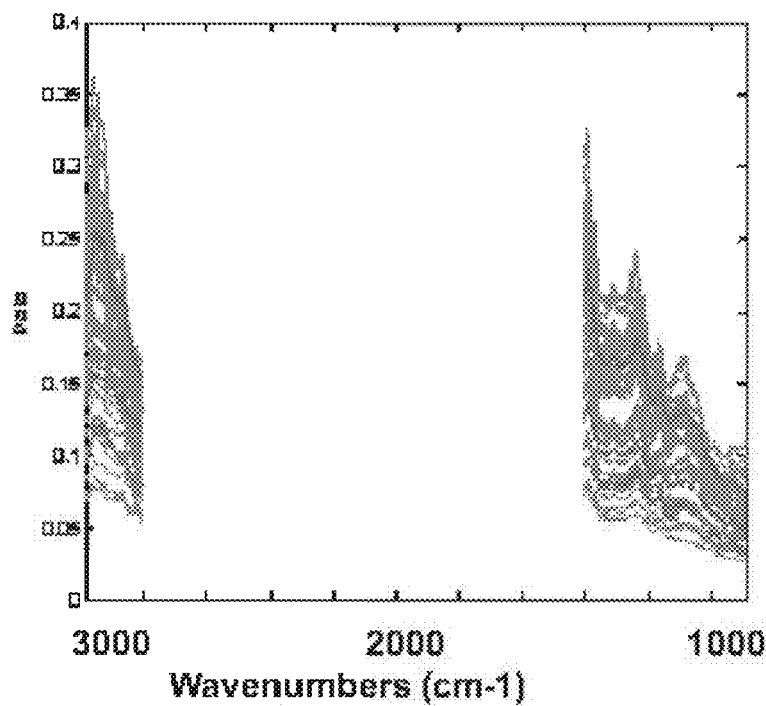
FIG. 27 is an IR absorption plot for the spectral window from 3000-2820 cm$^{-1}$ and 1400-900 cm$^{-1}$.

Lipid extracts from serum, or plasma or blood or a combination thereof in a solvent, such as methanol (MeOH) is typically processed according to the method of the present invention to generate the ATR-FTIR spectrum shown in FIG. 2 using the following steps:
  a) WB/Plasma/Serum is extracted using the same procedure as in section 1.1.
  b) WB/Plasma/Serum is mixed with an organic solvent. If emulsion is formed, sample should be centrifuged.
  c) 1-5 microliters of the extracting phase are taken with a micropipette and deposited on the ATR crystal.
  d) Sample is dried through different methods (Allowing to dry/using a drier or heat lamp)
  e) After drying, spectrum of the dry film is acquired.
  f) Cleaning of the crystal according to the General Procedure above.

Malaria as the Disease Agent

Malaria is caused by different species of *Plasmodium*. The different species of *plasmodium* have a different molecular phenotype and corresponding infrared spectra. Different species of Malaria causative agent are included in the Malaria reference database. To speciate or identify the different species of *plasmodium* typically one would use the following method first to identify that the person has malaria such as the following.

Accordingly, in a further embodiment of the method of detecting malaria in a blood sample according to the present invention, the method comprises the steps of:
  (i) creating a sample infra-red spectrum representative of the blood sample, the sample spectrum having one or more spectral components, each component having a wavenumber and absorbance value.
  (ii) providing a reference database of spectral models, each model having one or more database spectral components of a wavenumber and an absorbance value, wherein the database spectral components identify malaria, (iii) determining whether the reference database has one or more database spectral components corresponding to one or more sample spectral components, and (iv) compiling a list of corresponding database components identified.

In a further embodiment of the method of the present invention, to speciate and determine the causative agent of malaria into the various *Plasmodium* species, the method comprises the steps of:

(i) creating a sample infra-red spectrum representative of the blood sample, the sample spectrum having one or more spectral components, each component having a wavenumber and absorbance value.

(ii) providing a reference database of spectral models, each model having one or more database spectral components of a wavenumber and an absorbance value, wherein the database spectral components identify the different *Plasmodium* species such (as and not limited to) *Plasmodium falciparum, Plasmodium vivax, Plasmodium ovale curtisi, Plasmodium ovale wallikeri, Plasmodium malariae, Plasmodium knowlesi* or combinations thereof, (iii) determining whether the reference database has one or more database spectral components corresponding to one or more sample spectral components, and (iv) compiling a list of corresponding database components identified.

Experimental Results—Malaria

Experimental test carried out using the above methods have shown a correlation between the spectra and malaria parasite concentration in blood. Red blood cells (RBC) and whole plasma samples (WB) loaded with different concentrations of parasitemia (rings and trophocytes) were dried in glass fibre paper. The loading regime is summarised in Table 4:

TABLE 4

| Type of Blood Sample | Type of Parasitemia | Parasitemia (level of loading) |
| --- | --- | --- |
| RBC | CONTROL | 0 |
| RBC | CONTROL | 0 |
| RBC | CONTROL | 0 |
| RBC | CONTROL | 0 |
| RBC | CONTROL | 0 |
| WB | CONTROL | 0 |
| WB | CONTROL | 0 |
| WB | CONTROL | 0 |
| WB | CONTROL | 0 |
| WB | CONTROL | 0 |
| GF TR | GF TR | 0 |
| GF UNT | GF UNT | 0 |
| RBC | RING | 0.078125 |
| RBC | RING | 0.15625 |
| RBC | RING | 0.3125 |
| RBC | RING | 0.625 |
| RBC | RING | 1.25 |
| RBC | RING | 10 |
| RBC | RING | 10 |
| RBC | RING | 2.5 |
| RBC | RING | 5 |
| RBC | RING | 5 |
| WB | RING | 0.078125 |
| WB | RING | 0.15625 |
| WB | RING | 0.3125 |
| WB | RING | 10 |
| WB | RING | 2.5 |
| WB | RING | 5 |
| RBC | TROPHOCYTE | 0.078125 |

TABLE 4-continued

| Type of Blood Sample | Type of Parasitemia | Parasitemia (level of loading) |
| --- | --- | --- |
| RBC | TROPHOCYTE | 0.15625 |
| RBC | TROPHOCYTE | 0.3125 |
| RBC | TROPHOCYTE | 0.625 |
| RBC | TROPHOCYTE | 1.25 |
| RBC | TROPHOCYTE | 2.5 |
| RBC | TROPHOCYTE | 5 |
| WB | TROPHOCYTE | 0.078125 |
| WB | TROPHOCYTE | 0.15625 |
| WB | TROPHOCYTE | 1.25 |
| WB | TROPHOCYTE | 5 |

Figure 28:
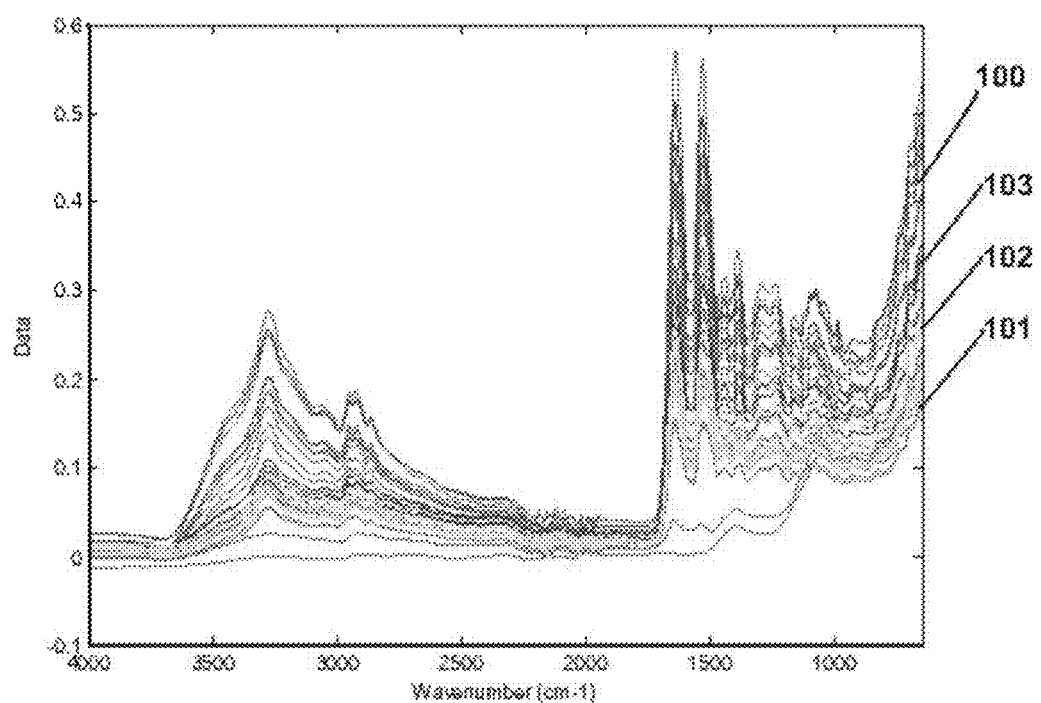
FIG. 28 is an IR absorption plot for the spectral window from 4000-0 cm$^{-1}$ for controls (100), and blood samples loaded with malaria paraseitemia (rings and trophocytes—RP (101), RNP (102) and TP (103)).

FIG. 28 is aa IR absorption spectrum of the control, RP, RNP and TP samples loaded with malaria as listed in Table 4. The naked eye cannot readily distinguish differences between the spectra of the control and the pathological samples.

Figure 29A:
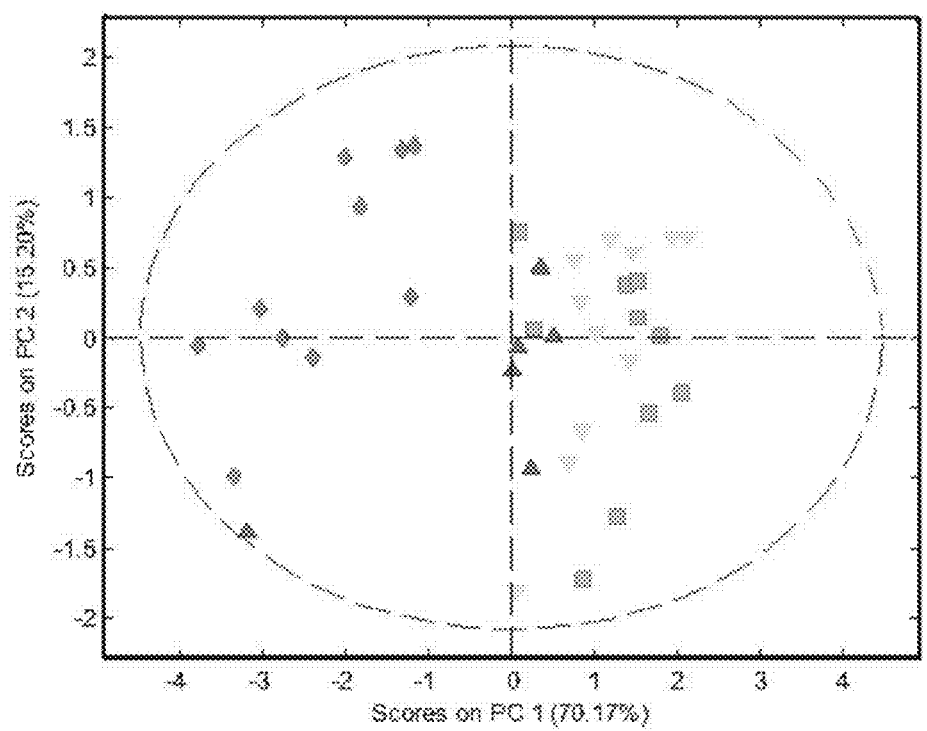
FIGS. 29A and 29B are plots in two different formats depicting the result of a multivariate analysis of the results depicted in FIG. 28, showing samples/scores of multiple SPC files for the samples in the region from 3116.19 to 2768.71 and 1828.46 to 852.91 cm$^{-1}$. (Control (◇), RP (□), RNP (▲), TP (▼) with the broken oval line indicating 95% confidence level across x and y axes, also marked in broken lines. PC1 (70.17%)(110) and PC2 (15.20%)(111) are included in FIG. 29B with depicts variables/loading for multiple SPC files.
Figure 29B:
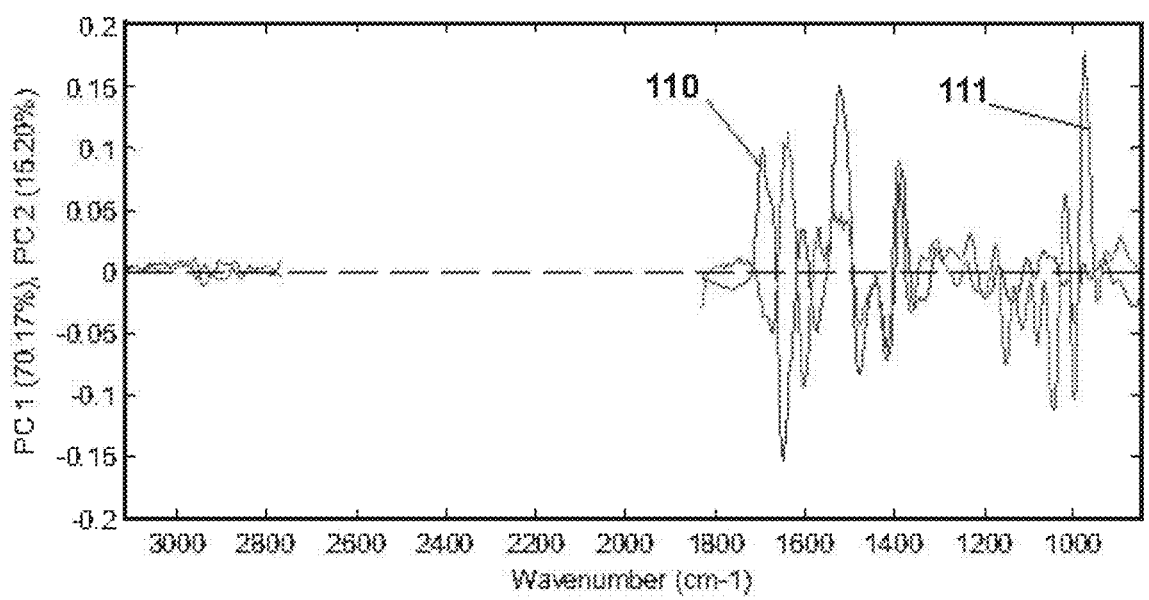

FIGS. 29A and 29B are plots in two different formats depicting the result of a multivariate analysis showing samples/scores of multiple SPC files for the samples in the region from 3116.19 to 2768.71 and 1828.46 to 852.91 $cm^{-1}$. Multivariate analysis is used to clarify differences or find hidden patterns. The method selected is principal components analysis (PCA), an unsupervised method (i.e., it does not take into account the classes, only uses the spectra) that projects the samples in new coordinates orientated in the directions of the variance.

Figure 30:
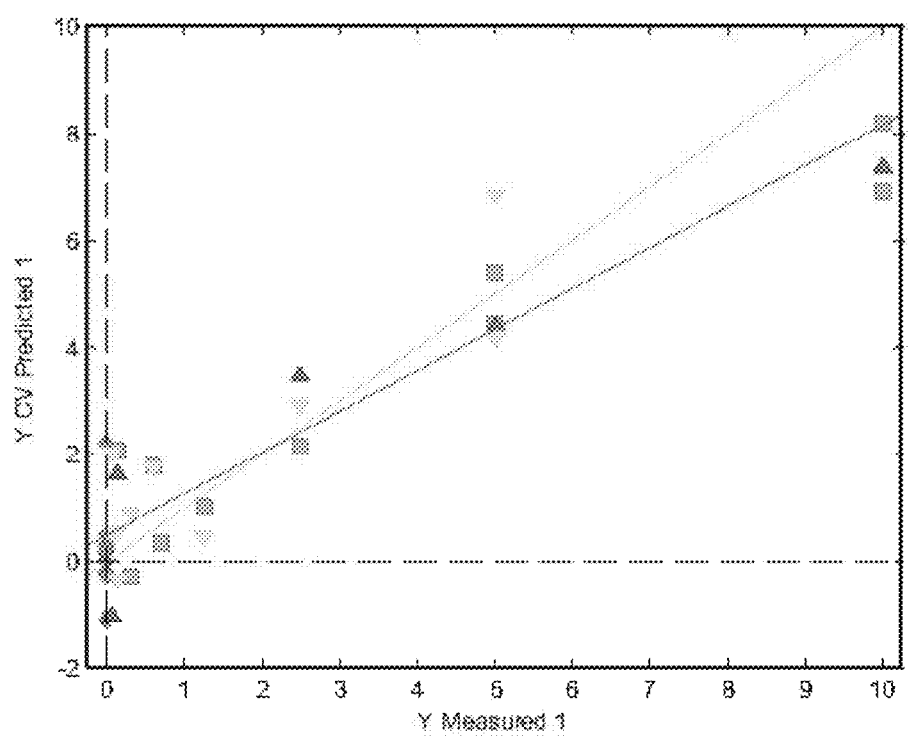
FIG. 30 is a partial least squares regression plot of predicted vs actual level of parasitemia in the samples depicted in FIG. 46. (Control (◇), RP (□), RNP (▲), TP (▼)).
Figure 31A:
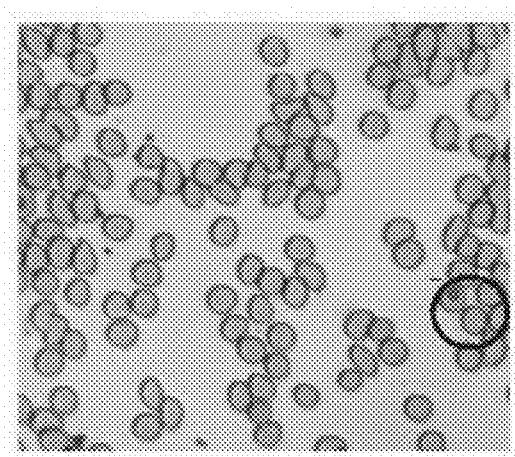
FIG. 31 illustrates visible images of cells that are stained (FIG. 31A) and IR images of untreated cells (FIG. 31B) based on mean spectra in the region 2500 to 4000 cm$^{-1}$.
FIG. 31C is a visual close up of two cells (marked A and B, circled in FIG. 31A) with corresponding IR images (FIG. 31D).
Figure 31B:
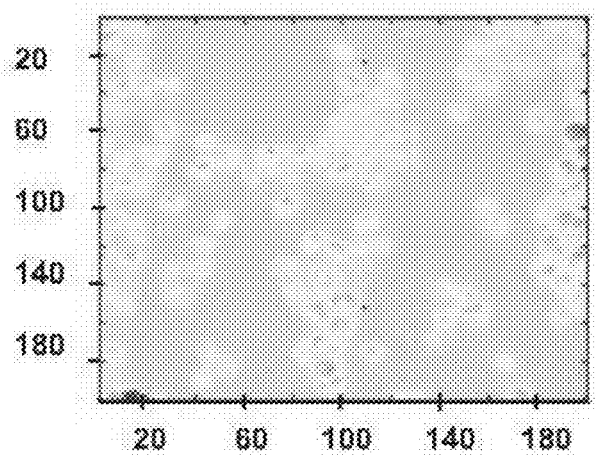
Figure 31C:
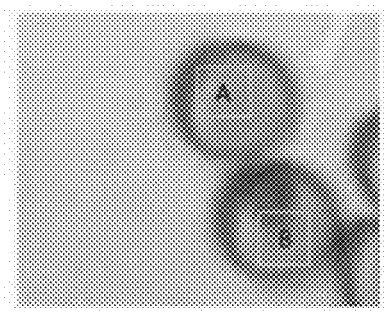
Figure 31D:
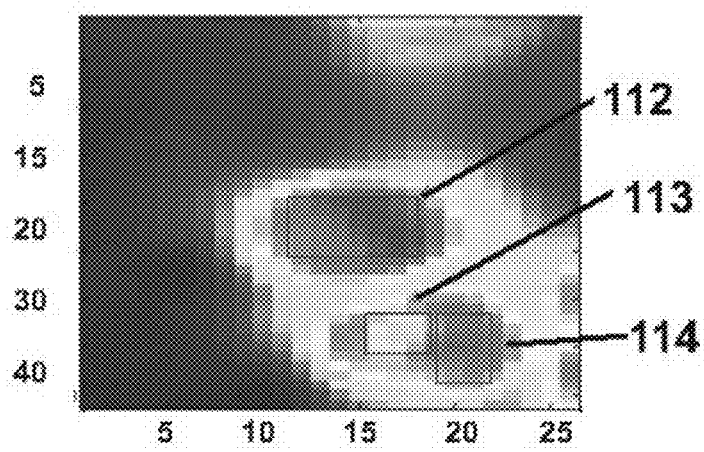

FIG. 30 is a partial least squares regression plot of predicted vs actual level of parasitemia in the samples. The regression analysis enables discrimination between high and low parasite loadings. Note that the method is linear, and covers several orders of magnitude.

Further experimental testing was carried out to see whether the IR signature of the malarial trophocyte on the RBC was maintained when dried in the paper. Ten RBC samples were loaded with 5% paraseitemia (trophocytes) and dried on normal filter paper. Twelve normal RBC samples were also created as controls.

The method of the present invention has also been used for detection in respect of samples known to contain *Plasmodium falciparum* and/or *Plasmodium vivax* by microscopy and PGR. The results using FTR demonstrated that the method was suitable for detection of infection by both malarial species and mixed infection.

Experimental Results—Detection of Malaria Using Images Obtained from Thin Smears of RBC in Glass Experimental investigations were undertaken to investigate the efficacy of the method of the present invention with respect to distinguishing between RBCs infected with 5% malarial trophozoites, an uninfected blood cells.

In this case Focal Plane Array was used, that is, FP spectroscopic imaging of thin blood smears on glass. After image acquisition the samples were stained with Giemsa stain for the visual detection of the trophozoites.

FIG. 31 shows visible images of cells that are stained (FIG. 31A) and IR images of untreated cells (FIG. 31B) based on mean spectra in the region 2500 to 4000 $cm^{-1}$. FIG. 31C is a visual close up of two cells (marked A and B, circled in FIG. 31*a*) with corresponding IR images (FIG. 31D). It is clear from these images that the density of the spectra is greater when the parasite is not present. PCA analysis reveals three areas—uninfected RBC areas (112),

*plasmodium* for the trophozoites (113) and a second uninfected area for the part of the infected RBC without the trophozoite (114).

Figure 32:
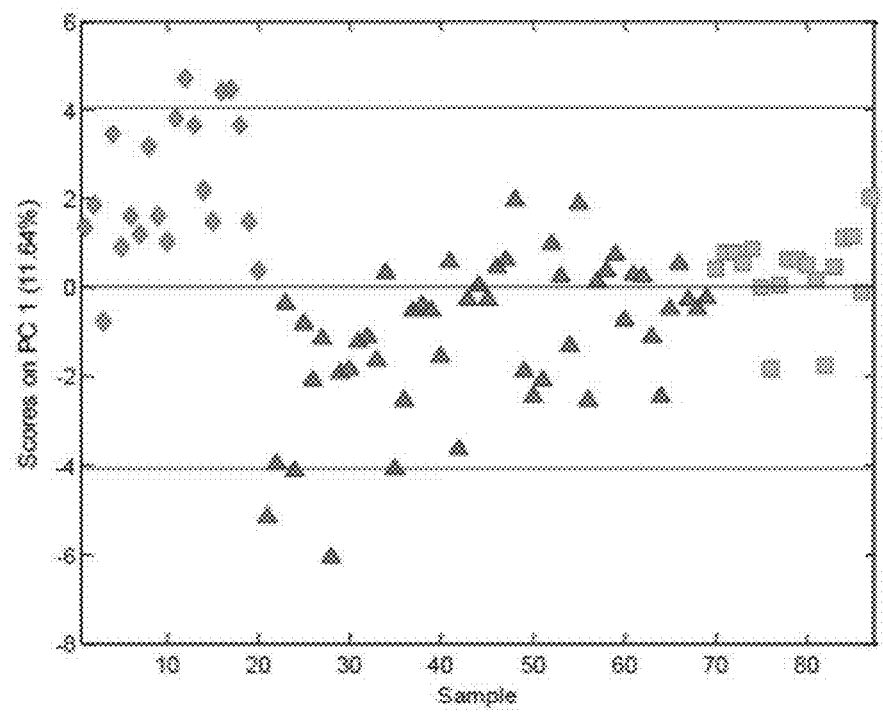
FIG. 32 illustrates a PCA corresponding to FIG. 31 for the *plasmodium* infected area (◇), the first uninfected are (▲) and second uninfected area (□).

The corresponding PCA is recorded in FIG. 32 for the *plasmodium* infected area (◊), the first uninfected are (▲) and second uninfected area (□). The 95% confidence level is marked in at −4 and 4.

Figure 33:
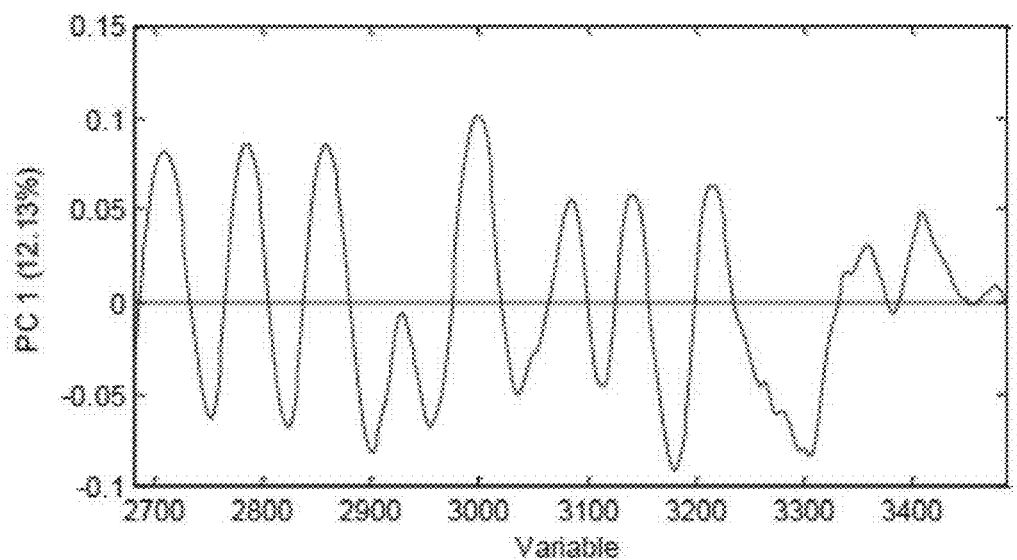
FIG. 33 is a variables/loading plot.
Figure 34:
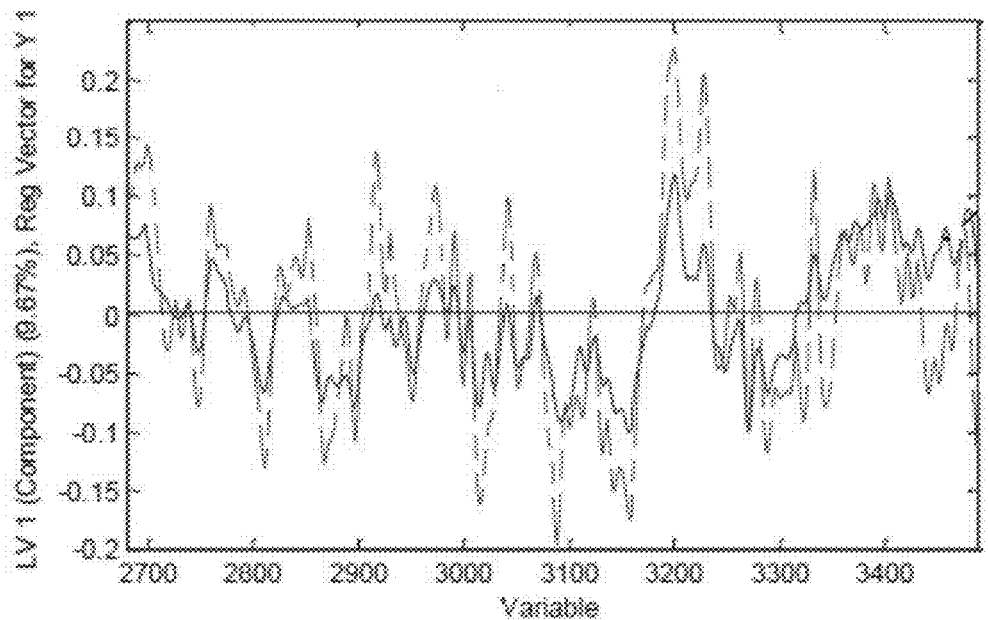
FIG. 34 illustrates a supervised model PLSDA (without derivative) was performed showing the LV 1 component (unbroken line) and Reg Vector for Y1 (broken line).

FIG. 33 is a variables/loadings plot. In order to more closely examine the differences, a supervised model PLSDA (without derivative) was performed and is illustrated at FIG. 34. The LV 1 component (unbroken line) and Reg Vector for Y1 (broken line) are shown. Although the regression vector is quite noisy, there is a shift at the 3300 $cm^{-1}$ band which is able to discriminate between infected and non-infected pixels.

Based on the aforementioned results the following methodology for the identification of paraseitemia in untreated RBC thin films on glass can be proposed:
(i) create a thin blood film,
(ii) carry out microscopic visual analysis and create a visual image,
(iii) create an FTIR image,
(iv)(a) model each pixel of the image in order to classify them as parasite or RBC,
(iv)(b) extract RBC means spectra, averaging the pixels of each RBC and investigate whether each RBC is infected or not.

Experimental Results—Hepatitis

Experimental tests carried out using the above methods have shows that it is possible to distinguish between plasma samples bearing different types of hepatitis.

Figure 35:
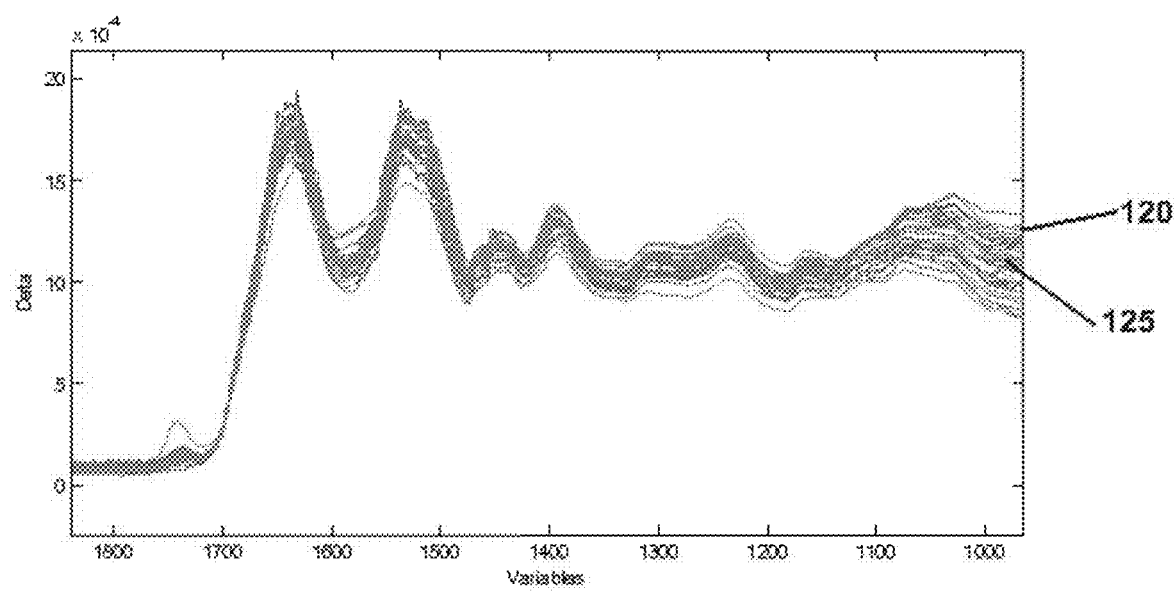
FIG. 35 is an IR spectrum for plasma samples bearing different types of hepatitis (Hepatitis B (120); Hepatitis C (125)).

For each sample, approximately 3 microliters of plasma bearing Hepatitis B (HB) and Hepatitis C (HC) was placed onto pre-cut glass filter paper and air-dried for 20 minutes. The glass paper with the dried plasma sample was then placed onto the crystal of a diamond ATR-FTIR window and a spectrum recorded at 8 $cm^{-1}$ with 50 scans co-added and ratioed against a background spectrum of air. The resulting spectrum is illustrated in FIG. 35.

Figure 36:
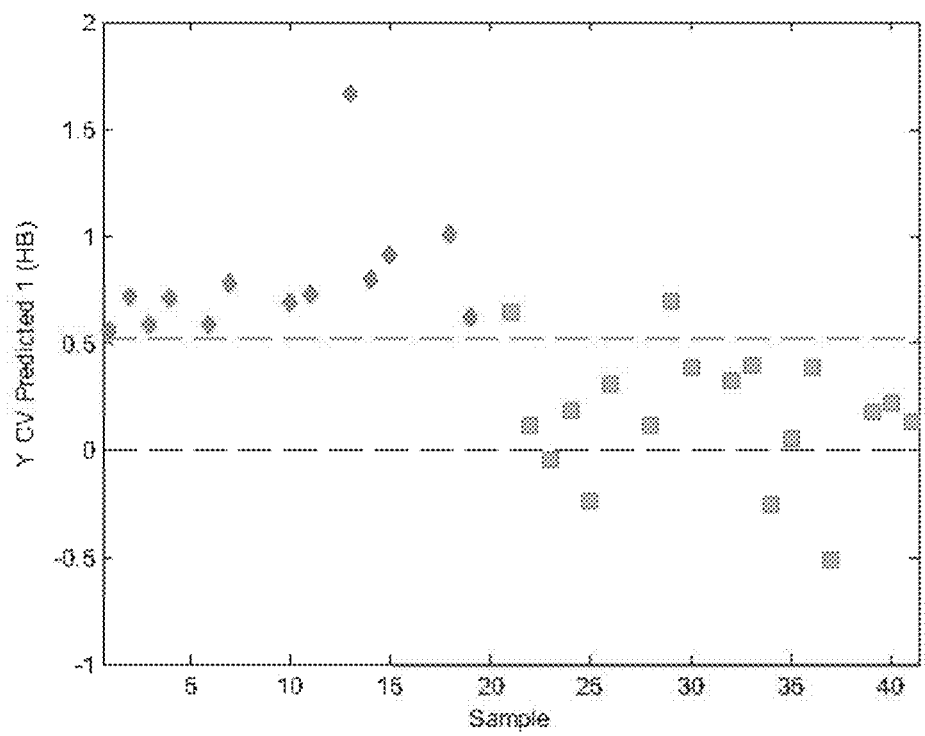
FIG. 36 is a partial least squares regression plot of predicted vs actual level of hepatitis in the samples (Hepatitis B (◇); Hepatitis C (□)).

FIG. 36 is a partial least squares regression plot of predicted vs actual level of hepatitis in the samples. The data analysis was carried out for the samples in the region from 1583.18 to 1492.13 $cm^{-1}$ and 1304.45 to 1120.49 $cm^{-1}$. The regression analysis enables discrimination between high and low parasite loadings and between HB and HC infection.

Experimental Results—Glucose & Urea

The previous experimental results illustrated spectral effects relating to IR energy absorbed directly by a disease agent in the form of parasitemia present in the blood. Experimental tests carried out using the method of the present invention have also know that it is possible to detect a disease agent indirectly, via the energy absorbed by other biological entities caused by the disease agent. For example, the disease agent may cause rises in glucose, urea or both.

Figure 37:
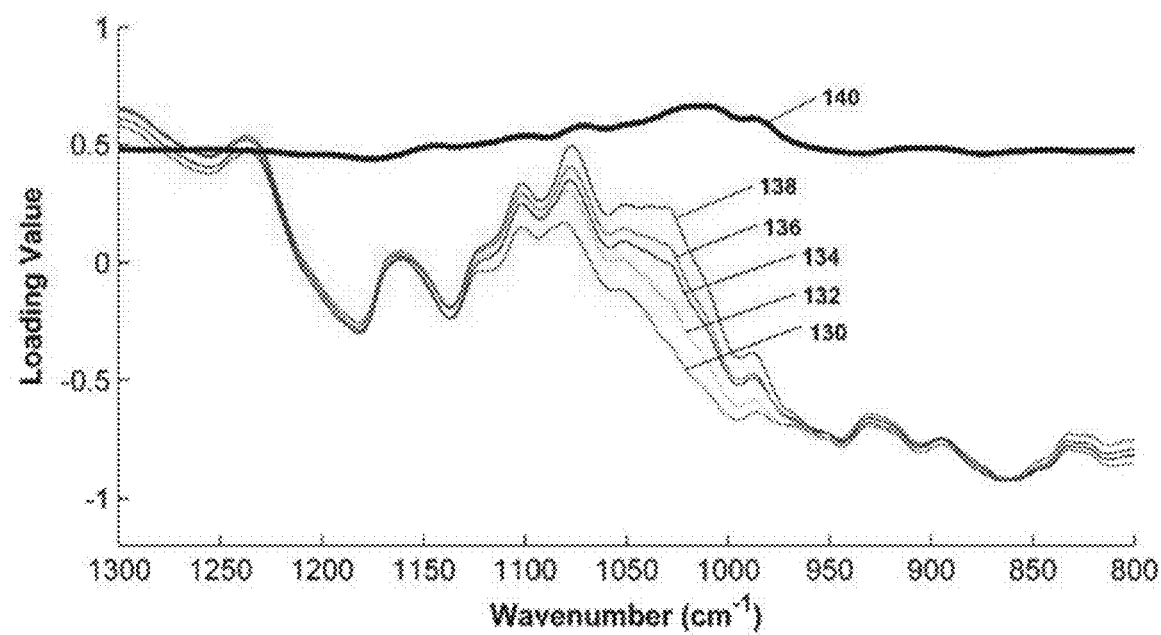
FIG. 37 is an FTIR spectrum for blood samples loaded with a range of concentrations of glucose and urea and dried on a glass fibre (100 mg/dl (130); 297 mg/dl (132); 490 mg/dl (134); 679 mg/dl (136); 865 mg/dl (138); neat glucose] (140)).

Blood samples were loaded with a wide range of concentrations of glucose and urea and dried on glass fibre. FIG. 37 illustrates the FTIR spectrum for the samples and illustrates the absorbance of glucose is proportional to the concentration of glucose in the sample.

Figure 38:
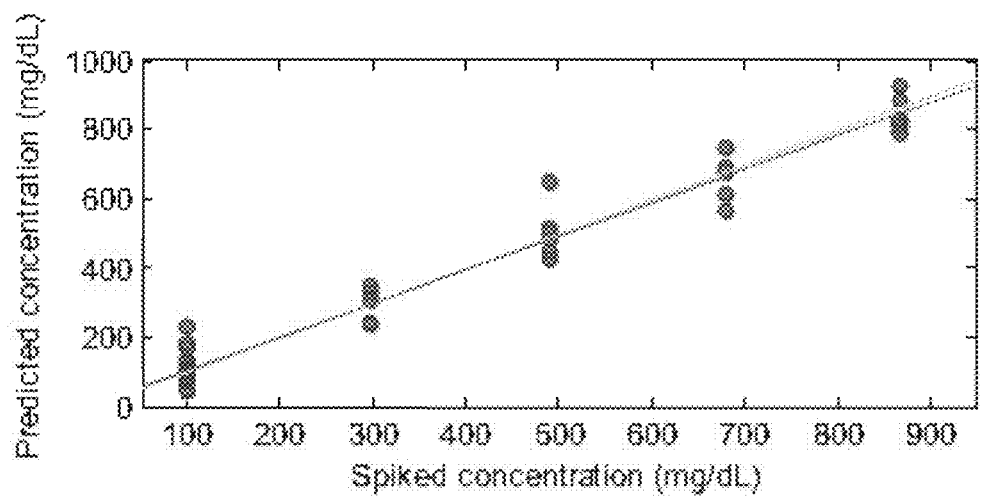
FIG. 38 is a partial least squares plot of the results for glucose as shown in FIG. 33. The unbroken line illustrates the best fit, and the broken line illustrates the 1:1 correlation between predicted and spiked correlations.
Figure 39:
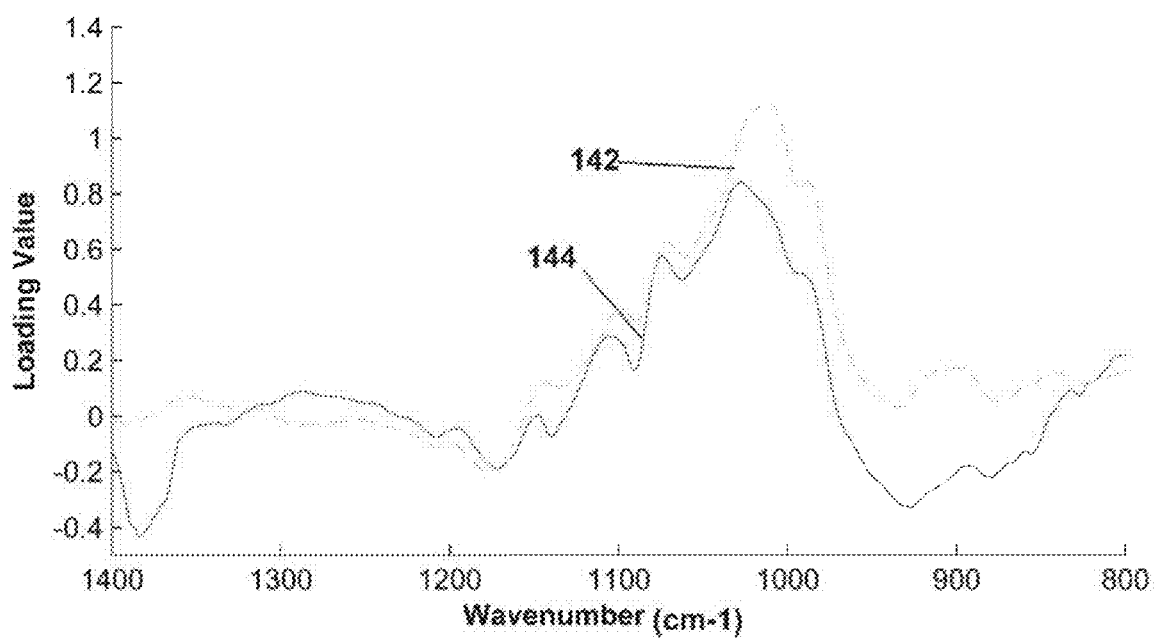
FIG. 39 is a standard IR spectrum for glucose.

FIG. 38 provides a partial least squares plot of the results. A regression vector was then correlated with the glucose standard spectrum as shown in FIG. 39.

Figure 40:
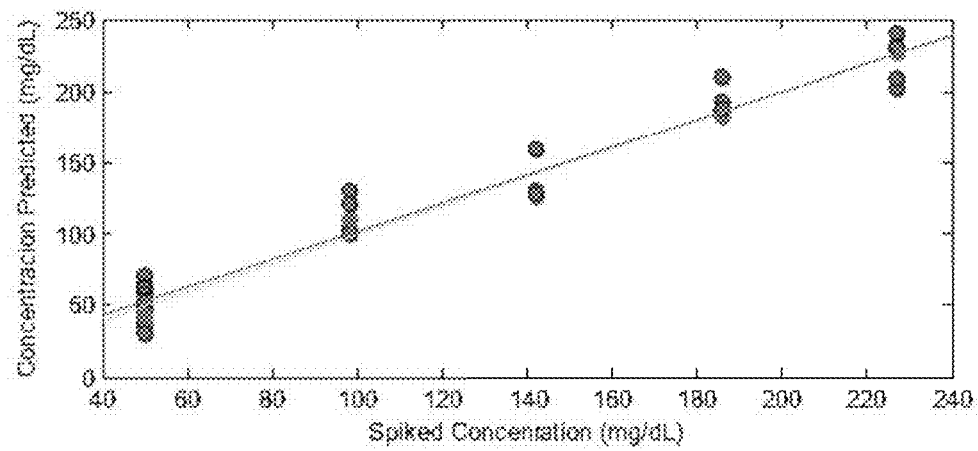
FIG. 40 is a partial least squares plot of the results for urea as shown in FIG. 33. The unbroken line illustrates the best fit, and the broken line illustrates the 1:1 correlation between predicted and spiked correlations.
Figure 41:
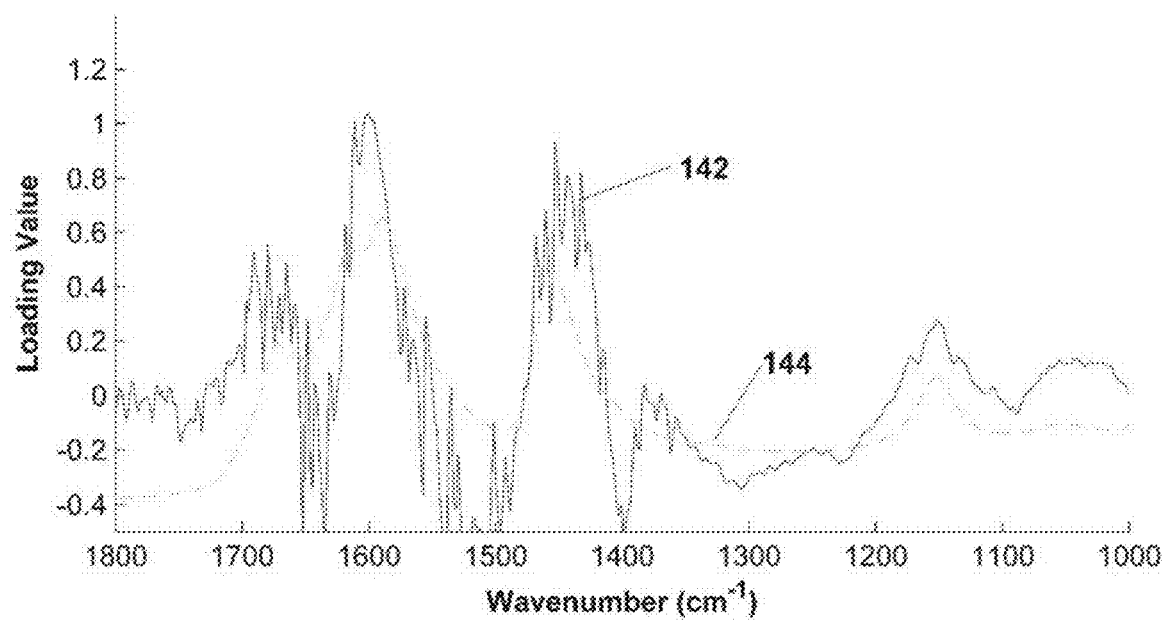
FIG. 41 is a standard IR spectrum of loading value against wavenumber.

A similar approach was taken with urea. FIG. 40 provides a partial least squares plot of the results. A regression vector was then correlated with the glucose standard spectrum as shown in FIG. 41.

Experimental Results—Quality Controls

Validation of the spectra can be carried out prior to inclusion into use of the aforementioned models. This ensures that an acquired spectrum has features similar to the features included in the model. It also ensures that technical issues are not going to interfere in the extraction of information from the model. For example, the following two methods of quality control were developed.

Quality Control—Model Independent

The first relies on quality control independent of the model that is, depending only on the database. The quality control focuses on trying to monitor excesses (or defects) of the different of components and interferences pertaining to the sample. The component relative concentration is calculated using an algorithm, and this concentration is compared with a threshold value. For example, a distribution of relative concentration values of the component can be created on the database. Then the portions of the distribution that tail off at the upper and lower ends can be used for defining the threshold. If the relative concentration of the component is outside the threshold, the spectrum does not pass the quality control.

Typically, the following three components are considered sequentially in this quality control method:
(i) Atmospheric interferences: Fluctuation of IR active atmospheric vapours between the background and sample measurements can cause negative and positive bands which are detected by using a positive and negative thresholds;
(ii) Solvent: The solvent (Water, MeOH) has not been properly eliminated; and
(iii) Sample: There is not enough sample on the crystal, for example, due to bad contact.

Quality Control—Model Dependent

The second quality control method is associated with the model and relies on measurement of the distance between the sample and the calibration samples in terms of the modelling. A typical example is the use of the $T^2$ and SQ residuals on a PLSDA and a 95% confidence interval.

For example, the quality control for a spectrum recorded could be carried out in the sequence (i) atmospheric interference (water), (ii) solvent (methanol), (iii) sample, and finally (iv) distance to the model. Typically this would correlate with results such as those in Table 5:

TABLE 5

| QC | Pre-processing | Calculation of relative concentration | Thresholds |
|---|---|---|---|
| $H_2O(g)$ | Normalization | Abs at 3846 $cm^{-1}$ − Abs at 3852 $cm^{-1}$ | <1.5 SD >1.5 SD |
| MeOH | Derivative | Abs at 1029 $cm^{-1}$ − Abs at 1033 $cm^{-1}$ | >1.5 SD |
| Sample | none | Absorbance at 1650 $cm^{-1}$ | <1.5 SD |

Figure 42:
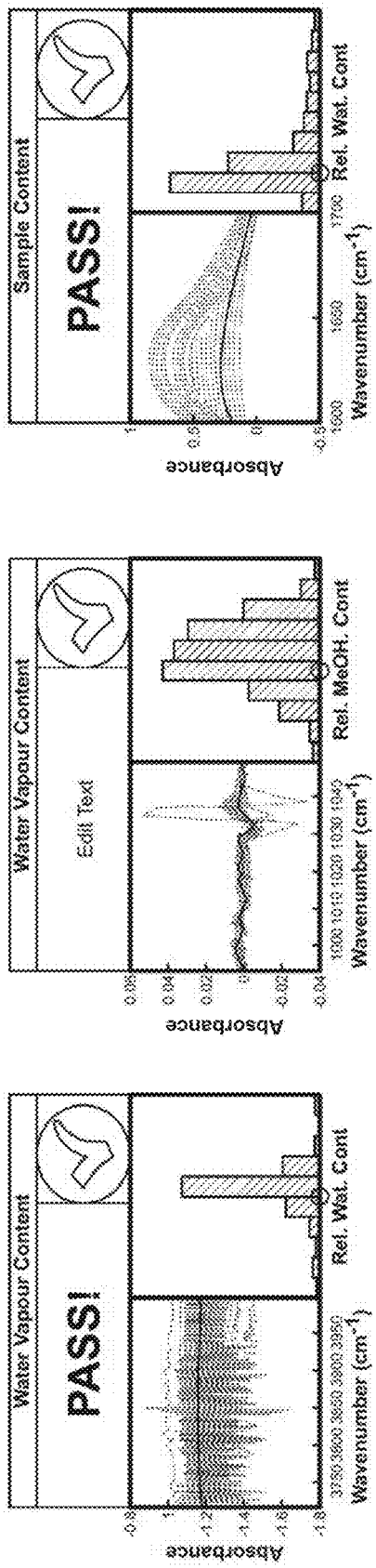
FIG. 42 is an example of a typical graphical user interface for spectral quality control that would be displayed to a user.

An example of a typical graphical user interface that would be displayed to the user is depicted in FIG. 42.

While this invention has been described in connection with specific embodiments thereof, it will be understood that it is capable of further modification(s). This application is intended to cover any variations uses or adaptations of the invention following in general, the principles of the invention and including such departures from the present disclosure as come within know or customary practice within the art to which the invention pertains and as may be applied to the essential features hereinbefore set forth.

As the present invention may be embodied in several forms without departing from the spirit of the essential characteristics of the invention, it should be understood that the above described embodiments are not to limit the present invention unless otherwise specified, but rather should be construed broadly within the spirit and scope of the invention as defined in the appended claims. The described embodiments are to be considered in all respects as illustrative only and not restrictive.

Various modifications and equivalent arrangements are intended to be included within the spirit and scope of the invention and appended claims. Therefore, the specific embodiments are to be understood to be illustrative of the many ways in which the principles of the present invention may be practiced. In the following claims, means-plus-function clauses are intended to cover structures as performing the defined function and not only structural equivalents, but also equivalent structures.

It should be noted that where the terms "server", "secure server" or similar terms are used herein, a communication device is described that may be used in a communication system, unless the context otherwise requires, and should not be construed to limit the present invention to any particular communication device type. Thus, a communication device may include, without limitation, a bridge, router, bridge-router (router), switch, node, or other communication device, which may or may not be secure.

It should also be noted that where a flowchart is used herein to demonstrate various aspects of the invention, it should not be construed to limit the present invention to any particular logic flow or logic implementation. The described logic may be partitioned into different logic blocks (e.g., programs, modules, functions, or subroutines) without changing the overall results or otherwise departing from the true scope of the invention. Often, logic elements may be added, modified, omitted, performed in a different order, or implemented using different logic constructs (e.g., logic gates, looping primitives, conditional logic, and other logic constructs) without changing the overall results or otherwise departing from the true scope of the invention.

Various embodiments of the invention may be embodied in many different forms, including computer program logic for use with a processor (e.g., a microprocessor, microcontroller, digital signal processor, or general purpose computer and for that matter, any commercial processor may be used to implement the embodiments of the invention either as a single processor, serial or parallel set of processors in the system and, as such, examples of commercial processors include, but are not limited to Merced™, Pentium™, Pentium II™, Xeon™, Celeron™, Pentium Pro™, Efficeon™, Athlon™, AMD™ and the like), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof. In an exemplary embodiment of the present invention, predominantly all of the communication between users and the server is implemented as a set of computer program instructions that is converted into a computer executable form, stored as such in a computer readable medium, and executed by a microprocessor under the control of an operating system.

Computer program logic implementing all or part of the functionality where described herein may be embodied in various forms, including a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, c, C++, JAVA, or HTML. Moreover, there are hundreds of available computer languages that may be used to implement embodiments of the invention, among the more common being Ada; Algol; APL; awk; Basic; C; C++; Conol; Delphi; Eiffel; Euphoria; Forth; Fortran; HTML; Icon; Java; Javascript; Lisp; Logo; Mathematica; MatLab; Miranda; Modula-2; Oberon; Pascal; Perl; PL/I; Prolog; Python; Rexx; SAS; Scheme; sed; Simula; Smalltalk; Snobol; SQL; Visual Basic; Visual C++; Linux and XML) for use with various operating systems or operating environments. The source code may defined and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and inter-networking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality where described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL). Hardware logic may also be incorporated into display screens for implementing embodiments of the invention and which may be segmented display screens, analogue display screens, digital display screens, CRTs, LED screens, Plasma screens, liquid crystal diode screen, and the like.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM or DVD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

"Comprises/comprising" and "includes/including" when used in this specification is taken to specify the presence of stated features, integers, steps or components but does not preclude the presence or addition of one or more other features, integers, steps, components or groups thereof. Thus, unless the context clearly requires otherwise, throughout the description and the claims, the words 'comprise', 'comprising', 'includes', 'including' and the like are to be construed in an inclusive sense as opposed to an exclusive or exhaustive sense; that is to say, in the sense of "including, but not limited to".

The invention claimed is:

1. A method of detecting hepatitis, comprising:
 obtaining a background spectrum from an empty clean ATR crystal;
 drying a plasma sample;
 acquiring a spectrum of the dried plasma using the ATR crystal; and
 performing a partial least squares discriminate analysis on the spectrum using wavenumber ranges from 1583.18 to 1492.13 $cm^{-1}$ and 1304.45 to 1120.49 $cm^{-1}$ to discriminate between Hepatitis B and Hepatitis C infection.

2. The method of claim 1, further comprising:
 placing the plasma sample on glass filter paper; and
 wherein drying the plasma sample comprises drying the plasma sample on the glass filter paper.

3. The method of claim 2, wherein drying the plasma sample comprises air-drying the sample for 20 min.

4. The method of claim 2, further comprising transferring the dried plasma sample from the glass filter paper to the ATR crystal.

5. The method of claim 1, further comprising:
 pipetting 1 to 5 microliters of plasma on a surface of the ATR crystal; and
 drying the plasma on the surface of the ATR crystal.

6. The method of claim 1, further comprising checking a wavenumber range from 3750 to 3950 $cm^{-1}$ to confirm sufficient drying of the plasma sample.

7. The method of claim 1, further comprising checking a wavenumber range from 1600 to 1700 $cm^{-1}$ to confirm sufficient contact of the dried plasma sample.

8. The method of claim 1, wherein identifying the presence of hepatitis C comprises reporting a probability of the presence of hepatitis C.

9. The method of claim 1, further comprising identifying the presence of hepatitis B based on a cv value of 0.5 or less.

10. The method of claim 9, wherein identifying the presence of hepatitis B comprises reporting a probability of the presence of hepatitis B.

* * * * *